(12) United States Patent
Wilden et al.

(10) Patent No.: US 10,046,117 B2
(45) Date of Patent: Aug. 14, 2018

(54) DRIVE MECHANISM FOR A DRUG DELIVERY DEVICE

(71) Applicant: SANOFI, Paris (FR)

(72) Inventors: Bjorn Wilden, Simmerath (DE); Stefan Bayer, Wurselen (DE); Philipp Zeitz, Aachen (DE); Wolfgang Pelzer, Kreuzau (DE)

(73) Assignee: Sanofi, Paris (FR)

( * ) Notice: Subject to any disclaimer, the term of this patent is extended or adjusted under 35 U.S.C. 154(b) by 202 days.

(21) Appl. No.: 14/782,742

(22) PCT Filed: Apr. 8, 2014

(86) PCT No.: PCT/EP2014/057002
§ 371 (c)(1),
(2) Date: Oct. 6, 2015

(87) PCT Pub. No.: WO2014/166920
PCT Pub. Date: Oct. 16, 2014

(65) Prior Publication Data
US 2016/0045666 A1    Feb. 18, 2016

(30) Foreign Application Priority Data

Apr. 10, 2013   (EP) .................................... 13163110

(51) Int. Cl.
*A61M 5/315*   (2006.01)
*A61M 5/20*    (2006.01)
*A61M 5/31*    (2006.01)

(52) U.S. Cl.
CPC .............. *A61M 5/315* (2013.01); *A61M 5/20* (2013.01); *A61M 5/31511* (2013.01); *A61M 5/31541* (2013.01); *A61M 5/31543* (2013.01); *A61M 5/31553* (2013.01); *A61M 5/31583* (2013.01); *A61M 2005/3126* (2013.01); *A61M 2205/581* (2013.01); *A61M 2205/582* (2013.01)

(58) Field of Classification Search
CPC ............ A61M 5/31553; A61M 5/3155; A61M 5/31533; A61M 5/20
See application file for complete search history.

(56) References Cited

U.S. PATENT DOCUMENTS

| 2007/0021715 | A1* | 1/2007 | Kohlbrenner | A61M 5/20 604/67 |
| 2009/0293870 | A1* | 12/2009 | Brunnberg | A61M 15/0078 128/203.12 |
| 2012/0253287 | A1* | 10/2012 | Giambattista | A61M 5/31553 604/189 |

FOREIGN PATENT DOCUMENTS

WO   WO 2006/069455   7/2006

* cited by examiner

*Primary Examiner* — Laura Bouchelle
*Assistant Examiner* — Tasnim M Ahmed
(74) *Attorney, Agent, or Firm* — Fish & Richardson P.C.

(57) ABSTRACT

Drive mechanism for a drug delivery device is disclosed. The drive mechanism includes an elongated housing extending in an axial direction. It includes a piston rod that operably engages with a piston of a cartridge to displace the piston in an axial distal direction. It includes a first dose indicating member that is rotatably supported on a longitudinal axis. It includes a second dose indicating member axially adjacent to the first dose indicating member and rotatably supported on the longitudinal axis. It includes a dose setting sleeve extending in an axial direction, rotatably engaged with the first dose indicating member and axially extending through the first dose indicating member to rotatably engage with the second dose indicating member.

16 Claims, 11 Drawing Sheets

A-A

B-B

C-C

D-D

E-E

F-F

G-G

H-H

J-J

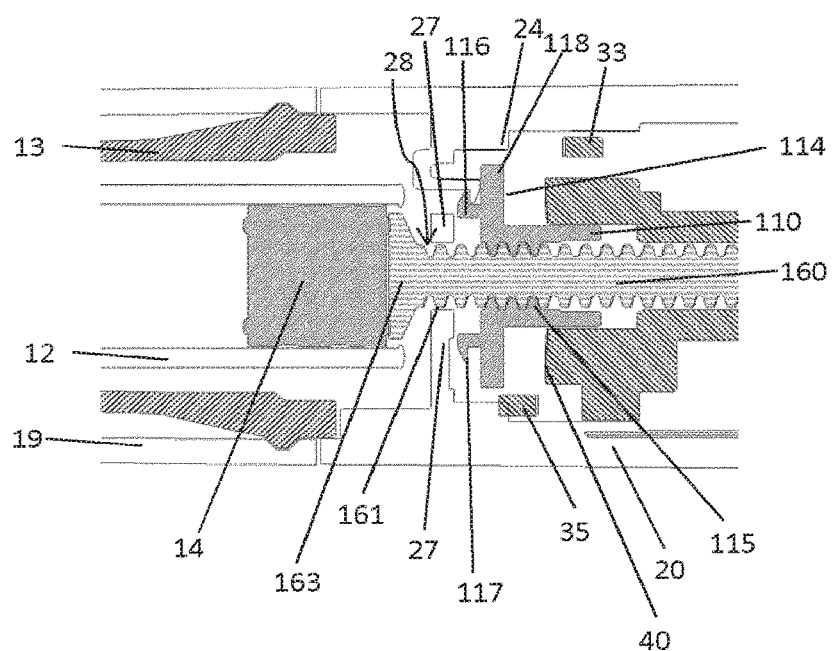
Fig. 12

K-K

DRIVE MECHANISM FOR A DRUG DELIVERY DEVICE

CROSS-REFERENCE TO RELATED APPLICATIONS

This application is a 371 U.S. National Phase Application of International Application Serial No. PCT/EP2014/057002, filed on Apr. 8, 2014, entitled "DRIVE MECHANISM FOR A DRUG DELIVERY DEVICE" which claims priority to European Application Serial No. 13163110.3, filed on Apr. 10, 2013 the entire contents of which are hereby incorporated by reference.

The present invention relates to a drive mechanism for a drug delivery device and to a respective drug delivery device. In particular, the invention relates to an injection device such like a pen-type injector inter alia comprising a single and/or a last-dose limiting mechanism.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

Drug delivery devices such like pen type injectors also provide a dose indicating mechanism which is operable to display the size of a set dose to a user. Typically, the housing of such drug delivery devices comprises a dose indicating window where a number representing the size of the dose shows up.

Especially with elderly or visually impaired patients, reading of such dose indicating numbers if sometimes difficult. With devices adapted for injection of e.g. insulin, typical dose sizes may vary between 0 and 120 IU (International Units) of insulin. Due to the rather compact design and limited geometrical dimensions of such drug delivery devices the size of such dose indicating numbers is fairly small. For visually impaired persons reading of such tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

It is another aim of the invention to visually indicate to a user that a dose setting and/or dose dispensing procedure is in progress and to provide a respective unequivocal and direct feedback to the user in addition to the visual indication of the size of the dose.

It is a further aim to provide a drug delivery device comprising such a drive mechanism and comprising a cartridge sealed with a piston and being operably engaged with a piston rod of such drive mechanism.

SUMMARY OF THE INVENTION

In a first aspect a drive mechanism for a drug delivery device is provided for dispensing of a dose of a medicament. The drive mechanism comprises an elongated housing extending in an axial direction. Typically, the housing is of substantially tubular or cylindrical shape that allows and supports gripping and operating of the drive mechanism or of the entire drug delivery device by one hand of a user.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge. Said expelled or dispensed amount correlates to the axial displacement of the piston as determined by the respective axially-directed displacement of the drive mechanism's piston rod.

Typically, the piston seals the cartridge in axial proximal direction. The piston rod of the drive mechanism serves to displace the piston of the cartridge in the axial direction. The piston rod is therefore operable to apply distally-directed thrust or pressure to the piston of the cartridge for displacing the same in distal direction for a predetermined distance that corresponds to the respective amount of the medicament, hence to the dose of the medicament to be dispensed.

Additionally, the drive mechanism comprises a first dose indicating member rotatably supported on a longitudinal axis. Typically, the longitudinal axis coincides with the center axis of the tubular shaped housing extending in axial direction. Hence, the longitudinal axis may extend parallel to the axial direction.

Moreover, the drive mechanism also comprises a second dose indicating member axially adjacent to the first dose indicating member and rotatably supported on the longitudinal axis. First and second dose indicating members may be of sleeve-like shape, wherein said sleeves are substantially identical in diameter. Additionally, first and second dose indicating members may be located axially adjacent. First and second dose indicating members may even axially abut.

Moreover, the drive mechanism also comprises a dose setting sleeve extending in axial direction. The dose setting sleeve is rotatably engaged with at least the first dose indicating member either directly or indirectly. The dose setting sleeve further axially extends into and/or through the first dose indicating member to rotatably engage with the second dose indicating member.

Here, first and second dose indicating members are mutually engaged only via the dose setting sleeve. Apart from an eventual axial and/or radial abutment of first and second dose indicating members, first and second dose indicating members are rotatably coupled with each other only by way of the dose setting sleeve.

In this way, first and second dose indicating members are designed and intended to visually indicate the size of a dose. But since neither the first dose indicating member is adapted to directly transfer a driving torque to the second dose indicating member nor the second dose indicating member is adapted to transfer a driving torque to the first dose indicating member, first and second dose indicating members can be designed in a rather filigree and hence space saving way.

By circumventing a direct torque-transmitting coupling of first and second dose indicating members, first and second dose indicating members can be rotated rather independent from each other only by way of their engagement with a common driving member, e.g. in form of the dose setting sleeve.

Typically, first and second dose indicating members are located inside a housing or below a cover portion of the drive mechanism which is provided with a dose indicating window, through which an outside facing display surface of first and second dose indicating members is discernible. Additionally, by providing at least two dose indicating members, various digits of an at least two-digit number can be displayed in an odometer-like way. Typically, the first dose indicating member may be indicative of single units of a set dose whereas the second dose indicating member may represent every tenth unit or decades of units, such like 10, 20, 30, 40 and so on.

While the first dose indicating member may be directly engaged with a continuously rotatable dose setting sleeve, the second dose indicating member may be engaged with said dose setting sleeve via some kind of transmission feature that serves to induce a stepwise incrementing or decrementing displacement of the second dose indicating member. In this way, the numbers present on the second dose indicating member and coinciding with the dose indicating window of the housing may rapidly jump towards an increasing or decreasing numeral during a dose incrementing or dose decrementing displacement of the dose setting sleeve.

According to an embodiment, the first dose indicating member comprises a first annular shaped display surface that flushes with a second annular display surface of the second dose indicating member. Having annular shaped display surfaces, the entirety of the circumference of the dose indicating members can be used to display consecutive numbers thereon. By arranging first and second annular shaped display surfaces in an axially flush manner, the various digits or numerals provided on first and second dose indicating members are concatenated by a user and may therefore represent any number between 0 and e.g. a maximum dose size, of e.g. 120 IU. Typically, the second dose indicating member is located distally offset from the first dose indicating member.

In order to support a well-defined flush mounted arrangement of first and second dose indicating members, respective dose indicating members may comprise axially at least one protruding portion engaging with at least one axial and/or radial recess, so that first and second dose indicating members mutually stabilize when arranged in axial abutment configuration. Typically, the first dose indicating member, in particular its radial outer rim-like portion supporting the first annular shaped display surface may axially protrude from a central portion of the first dose indicating member and may further engage with a correspondingly shaped radial and axial recess of a proximal and radially outwardly located portion of the second dose indicating member. In this way, a rather tilt- and/or cant-free mutual arrangement of first and second dose indicating members in the housing of the drive mechanism can be attained.

According to another embodiment, the first dose indicating member comprises a first central orifice axially flush with a second central orifice of the second dose indicating member. Hence, first and second dose indicating members not only axially flush with regard to their first and second annular shaped display surfaces but may also radially coincide and radially overlap with regard to their central orifice. In this way, the longitudinally or axially extending dose setting sleeve may penetrate through both, first and second central orifices of first and second dose indicating members.

In this way, the dose setting sleeve can be axially displaced relative to at least one of first and second dose indicating members, e.g. for switching the drive mechanism between a dose setting mode, in which the dose setting sleeve is located in a proximal dose setting position and a dose dispensing mode, in which the dose setting sleeve is located in a distal dose dispensing position.

At least one of the first and second dose indicating members may also rotatably engage with the dose setting sleeve via its respective central orifice. For instance, the central orifice may comprise a radially extending recess or protruding structure, such a geared structure, engaging with a correspondingly shaped radially extending recessed or protruding structure, hence a corresponding geared structure of the dose setting sleeve.

In other embodiments it is conceivable, that the dose setting sleeve slidably displaceable to at least one of first and second dose indicating members is indirectly rotatably coupled to the dose indicating members, e.g. via some kind of transmission gear located radially offset from the central orifice and the radial extent of the dose setting sleeve.

According to another embodiment, the dose setting sleeve is rotatably and axially connected to a drive sleeve serving as a distal extension of the dose setting sleeve. Moreover, the assembly of dose setting sleeve and drive sleeve extends through both, the first and through the second orifices of first and second dose indicating members. In this way, it is even conceivable, that the dose setting sleeve is rotatably engaged with the second dose indicating member via its axial extension in form of the drive sleeve. Generally, dose setting sleeve and drive sleeve may be integrally formed thereby forming a respective drive member comprising a dose setting sleeve portion and a drive sleeve portion.

In other embodiments where such a drive member is comprised of the dose setting sleeve fixed and connected with the drive sleeve, the mutual connection of dose setting sleeve and drive sleeve is adapted to transfer axial as well as rotational displacement of the dose setting sleeve to the drive sleeve and vice versa. The mutual interconnection of dose setting sleeve and drive sleeve is therefore comparable to an integral embodiment adapted to provide a permanent torque- and axial thrust-transmitting connection of dose setting sleeve and drive sleeve.

In embodiments, wherein the mentioned drive member comprises mutually engaged dose setting sleeve and drive sleeve, the interconnecting portion of dose setting sleeve and drive sleeve may be located distally from the second dose indicating member. It may be located between first and second dose indicating member or it may be located proximal to the first dose indicating member. Additionally, it is also conceivable, that the interconnecting portions of dose setting sleeve and drive sleeve at least partially overlaps with at least one of first and second orifices of first and second dose indicating members.

In particular by arranging for instance the second dose indicating member at least partially overlapping with the interconnecting portion of dose setting sleeve and drive sleeve, said mutual interconnection can be even secured or interlocked by the respective orifice. Mutual interconnection of dose setting sleeve and drive sleeve may be provided by a circumferentially extending groove engaging with a correspondingly shaped radial protrusion. Moreover, a longitudinally or axially extending recessed or protruding structure of one of dose setting sleeve and drive sleeve may engage with a correspondingly shaped and axially extending recessed or protruding structure of the other one of the dose setting sleeve and drive sleeve. In this way, a torque—as well as a thrust-transmitting interconnection of dose setting sleeve and drive sleeve can be established.

The two-part design of the drive member that requires permanent and mutual interconnection of dose setting sleeve and drive sleeve may be beneficial for the manufacture and assembly of the drive mechanism and/or of the respective drug delivery device.

According to another embodiment, the dose setting sleeve is rotatably engaged with the first dose indicating member via a first display wheel. Said first display wheel extends parallel and radially offset to the dose setting sleeve. With the first display wheel, a certain transmission ratio between the rotation of the dose setting sleeve and the first dose indicating member can be realized. Moreover, the first display wheel and its arrangement radially offset from the dose setting sleeve allows that the first central orifice of the first dose indicating member can be of rather even or smooth shape, which may be beneficial for a smooth and tilt-free axial displacement of the dose setting sleeve relative to the first dose indicating member.

According to another embodiment the drive sleeve rotatably engaged with the dose setting sleeve is further at least frequently rotatably engageable with the second dose indicating member via a second display wheel extending parallel and radially offset to the drive sleeve. By providing different display wheels for transmitting a driving torque of the drive sleeve or of the dose setting member to at least one of first and second dose indicating members, different transmission ratios for the first and second dose indicating members can be provided.

Given that the first dose indicating member is representing single units of 0-9 while the second dose indicating member represents decades of units of the set dose, the velocity of revolution of the first dose indicating member should be about ten times larger than the revolution velocity of the second dose indicating member. However, in case the first dose indicating member represents two series of numbers 0-9, the difference in revolution speed may be 5:1. First and second display wheels are typically radially sandwiched between the drive sleeve or the dose setting sleeve and the inside facing portion of the first and second dose indicating member's annular shaped display surfaces. In this way a rather compact and space-saving arrangement can be provided, which is generally beneficial for a handheld drug delivery device, such like an injection pen.

According to a further embodiment at least one of the first or second display wheels comprises two axially separated geared sections, wherein one of the two geared sections meshes with an outer gear of the dose setting sleeve or with a tappet of the drive sleeve. Furthermore, the other one of the two geared sections typically meshes with a central gear of the first or second dose indicating members.

By providing two geared sections, which may comprise different numbers of cogs or teeth, not only a varying transmission ratio between the dose setting sleeve, drive sleeve and at least one of first and second dose indicating members can be provided. Moreover, by means of axially separated geared sections of first and/or second display wheels, the outer gear of the dose setting sleeve can be arranged axially offset from the first dose indicating member, in particular from the central orifice of the first dose indicating member. In this way, a geared and torque transmitting engagement of the dose setting sleeve with the first dose indicating member can be located axially offset from the dose setting sleeve's central orifice, which may therefore be rather smooth and even shaped in order to support an axial sliding displacement of the dose setting sleeve relative to the first dose indicating member.

The same may also apply to the torque transmitting engagement of the drive sleeve or the dose setting sleeve with the second dose indicating member. Also here, by means of the second display wheel having axially separated geared sections, the shaft-like portion of dose setting sleeve or drive sleeve extending through the central orifice of the second dose indicating member may be rather smooth and even shaped to support an easy and smooth axial displacement of the dose setting sleeve and/or drive sleeve relative to at least one of first and second dose indicating members.

According to another embodiment, one axial end of at least one of the first and second display wheels is rotatably supported by the housing or by a base member connected to the housing. Moreover, an opposite axial end of the respective display wheel comprises a pin radially constrained in an annular and axially extending groove of first or second dose indicating members. By providing an annular and axially extending groove on at least one of the first or second dose indicating members the display wheel can be radially constrained and supported by the dose indicating member itself.

Additionally, since the display wheel is supported by the housing or by a base member, e.g. by means of an axially extending receptacle receiving a pin-like bearing portion of the housing or of the base member, the respective display wheel is radially and circumferentially fixed to the housing and/or to the respective base member. By further radially engaging with the annular groove of one of first and second dose indicating members, also a rotation of the dose indicating member may be further stabilized.

Additionally and according to another embodiment the at least one of the first and second display wheels is axially fixed or axially constrained between the housing and the at least one of the first and second dose indicating members. For example, the first display wheel may axially abut in proximal direction to a first base member rigidly attached to the housing and may further abut in distal direction with the bottom of the annular groove of the first dose indicating member. Since the second dose indicating member may axially abut to a distal end face of the first dose indicating member and since the second dose indicating member may be equally or symmetrically engaged with the second display wheel axially constrained between a distally facing side of the second dose indicating member and a proximal facing portion of e.g. a second, distal base member, first and second dose indicating members can be axially constrained and axially fixed relative to said first and second base members and hence to the housing of the drive mechanism via their respective first and second display wheels.

Respective first and second base members may further serve as a mounting base for assembling the first display wheel, the dose setting sleeve and the first dose indicating member to the first base member while the drive sleeve, the second display wheel and the second dose indicating member may be assembled to the second base member. Then, in a final step of assembly, the two preconfigured base members may be mutually assembled, thereby establishing a mutual torque-transmitting as well as axial thrust-transmitting engagement of dose setting sleeve and drive sleeve.

First and second base members may be mutually engaged or may be assembled and fixed to different portions of a common housing of the drive mechanism or of the drug delivery device. At least by assembling first and second base members in the housing first and second dose indicating members are axially fixed relative to the housing via the axial engagement with the torque-transmitting first and second display wheels while the dose setting sleeve and/or the drive sleeve may be axially displaceable relative to said base members, the housing and hence to first and second dose indicating members.

Typically, the first base member is located proximally offset from the second base member. Therefore, the first base member may also be denoted as the proximal base member while the second base member represents a distal base member.

According to another embodiment at least the dose setting sleeve is axially displaceable relative to at least one of first and second dose indicating members between a proximal dose setting position and a distal dose dispensing position. Typically, the dose setting sleeve but also the drive sleeve may comprise a diameter-reduced shaft portion by way of which the dose setting sleeve or the drive sleeve may extend through at least one of first and second dose indicating members. By axially displacing the dose setting sleeve, typically against the action of a retention spring element, the drive mechanism can be switched between a dose setting mode, in which the dose setting sleeve is rotatable for setting of a dose, and a dose dispensing mode, in which the drive sleeve is rotatable to apply and to transfer a driving force to the distally advancing piston rod.

Typically, since dose setting sleeve and drive sleeve are permanently rotatably and axially engaged, drive sleeve as well as dose setting sleeve experience a dose incrementing rotation for setting and increasing of a dose during dose setting and further experience an oppositely directed dose decrementing rotation during a dose dispensing procedure. By having a tappet radially outwardly extending on the drive sleeve meshing with a geared section of the second display wheel, a stepwise and discrete rotational displacement of the second display wheel can be realized as the drive sleeve continuously rotates.

Here, sections of first and/or second display wheels as well as the outer gear of the dose setting sleeve or the radially outwardly extending tappet of the drive sleeve comprise such an axial extension, that the geared engagement and rotational coupling of dose setting sleeve and drive sleeve with both, first and second dose indicating members is always retained, irrespective on whether the dose setting sleeve or drive sleeve are located in the proximal dose setting position or in the distal dose dispensing position.

According to another embodiment, the housing and/or the base member comprise a radially recessed or radially protruding retaining structure to engage with a corresponding radially protruding or radially recessed structure of the second dose indicating member. By means of mutually corresponding protruding and recessed structures of the retaining structure of the housing and/or the base member and the second dose indicating member, the second dose indicating member can be rotatably secured to the housing or to the base member once it has been stepwise rotated in a dose incrementing or dose decrementing direction.

The retaining structure is of particular benefit since the second dose indicating member is only frequently, hence non-permanently engaged with the dose setting sleeve or with the drive sleeve. It is particularly due to the at least one or several but circumferentially separated tappets of the drive sleeve, that the second display wheel is only occasionally engaged in a torque transmitting way with the drive sleeve. If the at least one drive sleeve's tappet is out of engagement with the second display wheel, the retaining structure serves to prevent a self-actuating rotational displacement of the second dose indicating member which may otherwise easily occur.

The retaining structure may comprise various radially inwardly extending protrusions or radially outwardly extending recesses provided on an inside facing portion of the base member or of the housing. The retaining structure is typically of annular shape and respective recesses or protrusions are arranged on the circumference of said annular shape in a regular and equidistant manner. Typically, the distance between adjacently located protrusions or recesses of the retaining structure correspond to the number of radially outwardly extending tappets of the drive sleeve and further corresponds with the transmission ratio provided by the second display wheel, which is geared with the second dose indicating member and which is further engageable with the tappet of the drive sleeve.

According to another embodiment the drive mechanism also comprises a third dose indicating member rotatably supported on the longitudinal axis and comprising a third annular shaped display surface to visually indicate a zero or maximum dose configuration. The third dose indicating member may be located axially offset from the first and second dose indicating members and may feature at least one indicator, such like a symbol or a colored portion visually indicating to a user that either a dose setting or dose dispensing procedure is actually in progress or that a maximum dose size has just set. In particular, the third dose indicating member is operable to visually indicate to the user, that the drive mechanism is ready to use. Moreover, at the end of a dose dispensing procedure, when the drive mechanism returns into an initial configuration, the third dose indicating member may change its visual appearance, e.g. through a respective window of the housing or of a drive mechanism's cover.

In a further embodiment, the third dose indicating member comprises an inwardly facing geared rim meshing with a radially outwardly extending tappet of the first display wheel. In this way, the first display wheel does not only serve to transfer a driving torque to the first dose indicating member but is also operable to induce a discrete and stepwise rotational displacement of the third dose indicating member.

Implementation of a tappet of the first display wheel engaging with a geared rim of the third dose indicating member is of particular benefit for that the third dose indicating member at maximum experiences a rotational movement smaller than a complete revolution while the first display wheel may rotate and revolve numerous times, in particular during setting and/or dispensing of a maximum dose of the medicament. By means of the tappet engaging with the third dose indicating member's geared rim, a rather large transmission ratio can be implemented for that the particular indicator of the third dose indicating member that shows up in the respective indicating window is unequivocal for each dose size actually set.

According to another embodiment, the third dose indicating member comprises an annular and radially inwardly facing retaining structure engaging with a radially outwardly extending retaining member of the housing or of the base member. In a similar way as already described in regard to the retaining structure for securing the second dose indicating member, also the third dose indicating member can be rotatably secured to the housing or to the base member for inhibiting a self-actuated rotation of the third dose indicating member when the tappet of the first display wheel is out of engagement with the inwardly facing geared rim of the third dose indicating member.

Moreover, and according to another embodiment, the first and the second dose indicating members at least in sections axially and radially abut. Typically, the annular shaped recesses of first and second dose indicating members may face in opposite directions, so that first and second dose indicating members axially and mutually abut with the plain or even shaped bottom portion of respective grooves. Additionally, the annular shaped display surface of at least one of first and second dose indicating members may axially extend from the respective member in order to radially overlap with a correspondingly shaped stepped down portion of the adjacently located first or second dose indicating member.

According to another aspect, the invention also relates to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The drive mechanism particularly serves to displace a piston rod in axial direction for the purpose of dispensing of a dose of a medicament. In addition, the drive mechanism typically comprises at least one component being part of and having a function in one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—

(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which:

FIG. 12 shows a longitudinal and enlarged cross section of the drive wheel engaging with the piston rod.

DETAILED DESCRIPTION

Figure 1:
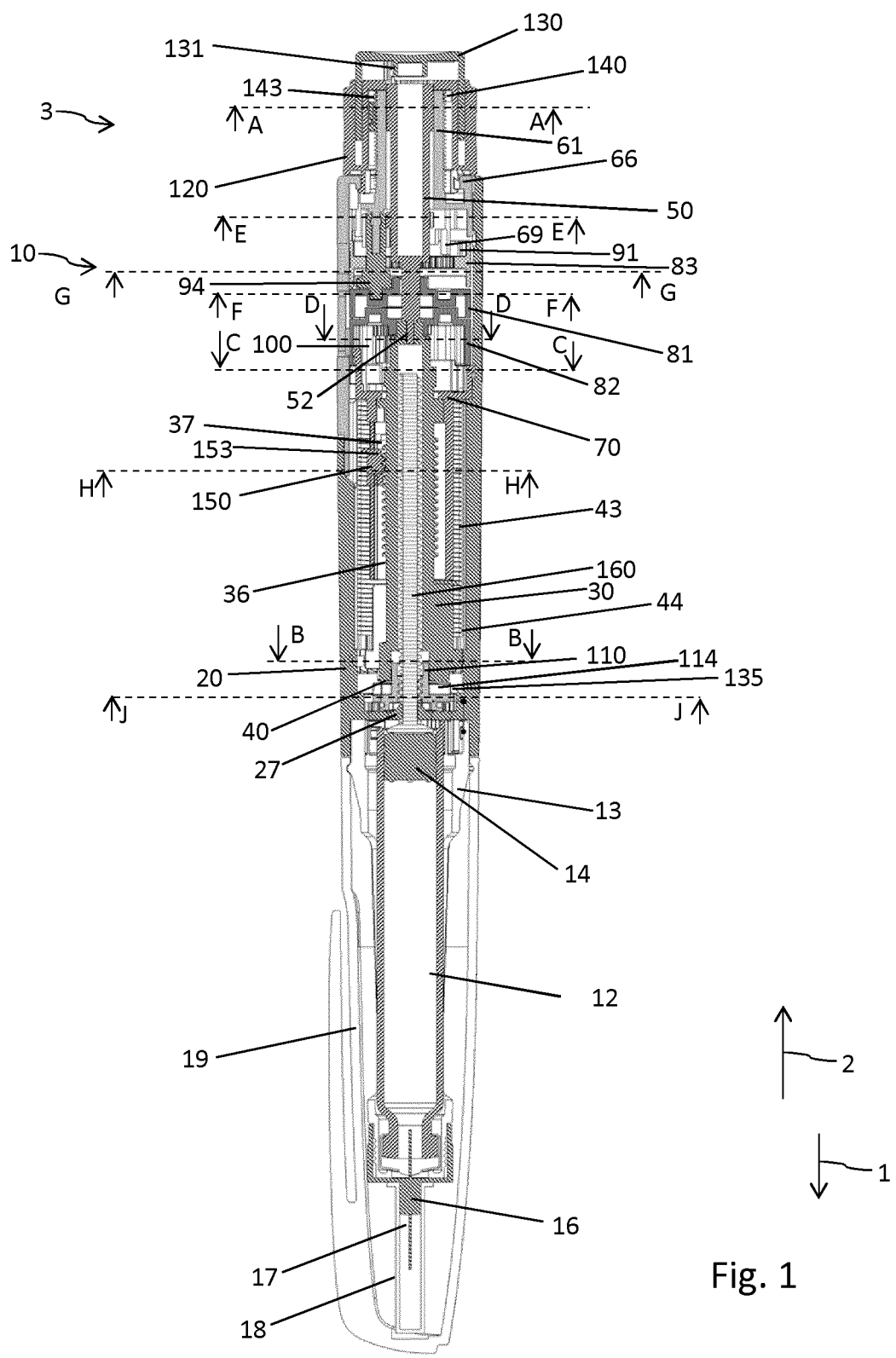
FIG. 1 schematically illustrates the assembled drive mechanism in a pen-type drug delivery device in a longitudinal cut, FIG. 2 perspectively illustrates an exploded view of the complete drug delivery device and its various components.
Figure 2:
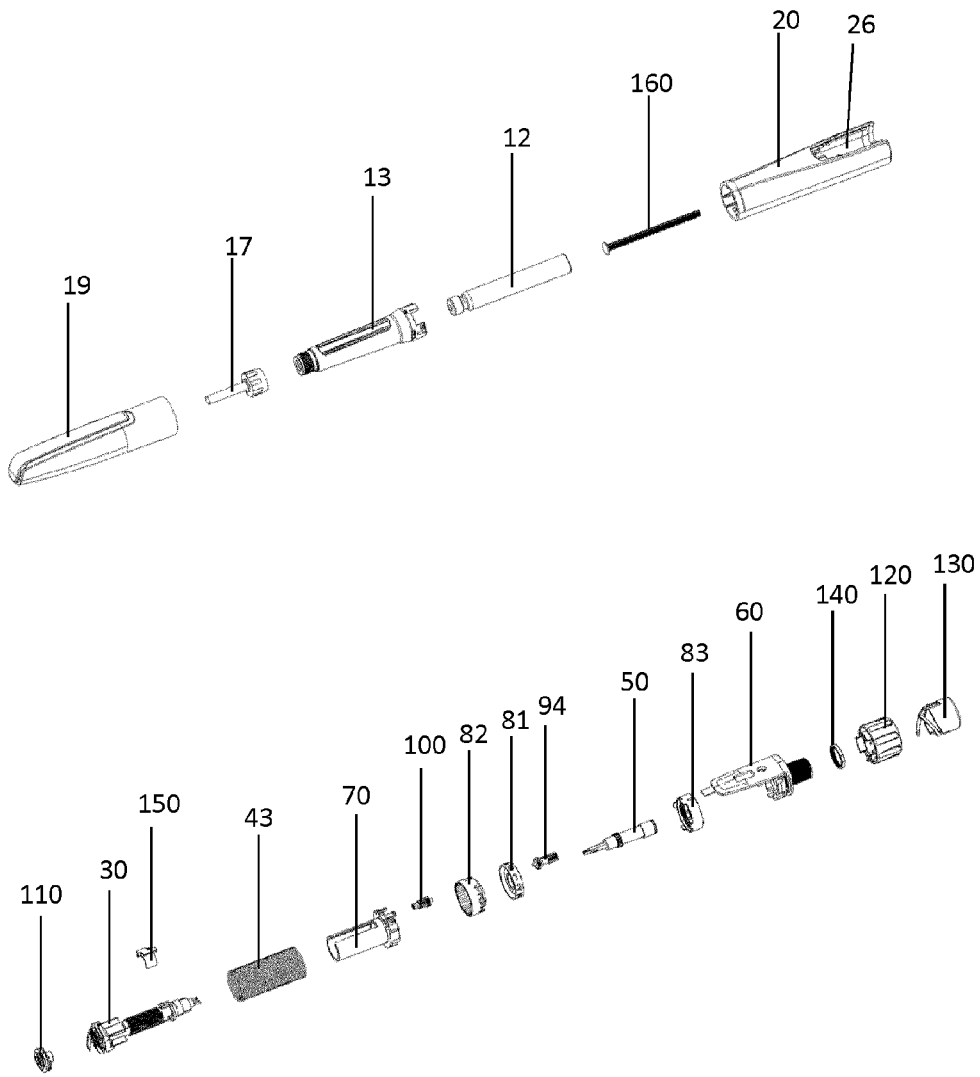

In FIGS. 1 and 2, the complete drug delivery device 10 is illustrated in a longitudinal cross section cut and in an exploded view. The drug delivery device 10 is of pen-injector type and comprises a substantially cylindrical and axially elongated shape. Throughout the Figures the axial distal direction is denoted with reference number 1 and the opposite proximal direction is denoted with reference number 2. The drug delivery device 10 comprises a drive mechanism 3 having comprising a proximal housing 20 or being assembled in a respective body 20 of the drug delivery device 10.

In distal direction the housing 20 is connected with a cartridge holder 13 which is adapted to accommodate and to receive a cartridge 12 containing the medicament to be dispensed by the drug delivery device 10 by way of its drive mechanism 3. The cartridge 12 typically comprises a vitreous barrel of cylindrical or tubular shape and is sealed in distal direction 1 by a pierceable sealing member, such like a septum.

In proximal direction 2, the cartridge 12 is sealed by means of a piston 14 slidably arranged in the barrel of the cartridge 12. The piston 14 typically comprises an elastomeric material, by way of which the proximal end of the cartridge 12 can be effectively sealed in a fluid- and gas-tight manner. The piston 14 of the cartridge 12 is to be operably engaged with a distal end of a piston rod 160 of the drug delivery device's 10 drive mechanism 3. A distally directed displacement of the piston 14 typically induced and governed by the piston rod 160 leads to a respective build up of a fluid pressure inside the cartridge 12. When the distal outlet of the cartridge 12 is connected with e.g. a needle assembly 16 as illustrated in FIG. 1, a predefined amount of the liquid medicament, which equals a previously set dose of the medicament, can be expelled from the cartridge 12 and can be dispensed via an injection needle 17 of the needle assembly 16.

As illustrated in FIG. 1, the needle assembly 16 comprises the double-tipped injection needle 17. The needle assembly 16 is typically removably arranged on a distal end portion of the cartridge holder 13. Here, a distally located socket of the cartridge holder 13 and the needle assembly 16 comprise mutually corresponding threads to screw the needle assembly 16 onto the cartridge holder 13 in a releasable and removable way.

The cartridge holder 13 and hence the cartridge 12 assembled therein is to be protected and covered by a removable protective cap 19. Prior to setting and/or dispensing of a dose, the protective cap 19 as well as an inner needle cap 18 of the needle assembly 16 have to be removed. After dispensing or injecting of the medicament, e.g. into biological tissue, the needle assembly 17 is typically to be disconnected from the cartridge holder 13 and is to be discarded.

The drive mechanism 3 as illustrated in the various FIGS. 3-19 comprises numerous functional and mechanically inter-engaging components by way of which a dose of variable size can be set and subsequently dispensed. The drive mechanism 3 is of semi-automated type. It comprises a means for storing mechanical energy during a dose setting procedure. Said mechanical energy is then usable for driving the piston rod in distal direction 1 during a dose dispensing procedure. Consequently, it is the device 10 and the drive mechanism 3 that provide mechanical energy and a driving force or driving torque to conduct an injection procedure. Consequently, an injection force does not have to be provided by the user during the dose dispensing process.

Does dispensing requires distally directed advancing of the piston rod 160 relative to the cartridge 12, hence relative to the cartridge holder 13 and relative to the housing 20. The drive mechanism 3 comprises a longitudinally extending hollow shaped drive sleeve 30 that is axially displaceable relative to the housing 20 for switching the drive mechanism 3 between a dose dispensing mode and a dose setting mode. The drive sleeve 30 is rotatably supported on a longitudinal axis 4 that may coincide with the center of the piston rod 160.

Figure 4:
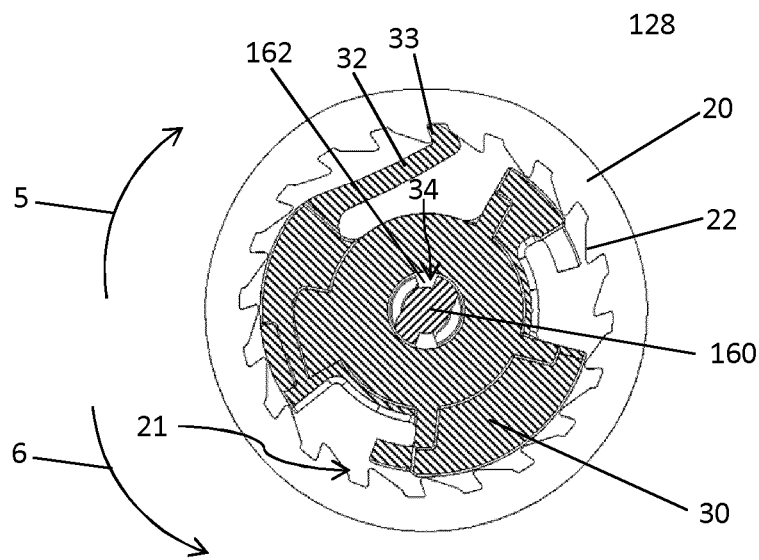
FIG. 4 shows a cross-section along B-D according to FIG. 1.
Figure 6:
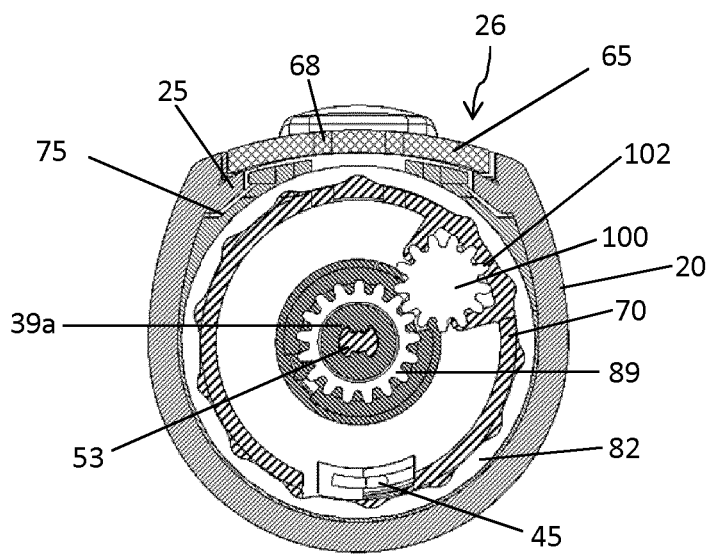
FIG. 6 shows a cross-section through the device along D-D according to FIG. 1.

The drive sleeve 30 is further connected with a spring element 43 featuring a helical shape and acting as a torsion spring. As illustrated in FIGS. 1 and 4, a distal end 44 of the helical spring element 43 is connected with a distal end portion of the drive sleeve 30 while an opposite, proximal end 45 of the helical spring element 43 is connected to a distal base member 70 as illustrated in FIG. 6. The base member 70 is fastened and unmovably fixed to the housing 20. In embodiments without a base member 70 the proximal end 45 of the helical spring element 43 may also be connected to a portion of the housing 20.

As indicated in FIG. 4 the drive sleeve 30 is rotatable in a dose incrementing direction 5 against the action of the helical spring element 43. For setting of a dose, hence for increasing a dose to be set, the drive sleeve 30 rotates in dose incrementing direction 5, thereby straining and biasing the helical spring element 43. In order to store respective mechanical energy in the drive mechanism 3, the drive sleeve 30 is rotatably engaged with the housing 20 by means of a ratchet member 32. The ratchet member 32 comprises an arc-shaped and resiliently deformable circumferentially extending portion featuring a radially outwardly extending catch portion or protrusion 33 that is adapted to engage with a correspondingly shaped first toothed profile 21 located at an inwardly facing sidewall portion of the housing 20.

As shown in FIG. 4, the catch portion or protrusion 33 of the drive sleeve's 30 ratchet member 32 positively engages with consecutive ratchet teeth 22 of the first toothed profile 21. In this way, the drive sleeve 30 can be rotatably secured to the housing 20 at least when located in its proximal dose setting position. The ratchet member 32 is adapted to prevent a self-actuating rotation of the drive sleeve 30 in dose decrementing direction 6 under the effect of the helical spring element 43.

However, the shape of the ratchet member's 32 catch portion 33 and the shape or slope of the various ratchet teeth 22 are designed such that the drive sleeve 30 may also be rotated in a dose decrementing direction 6 if a respective torque above a predefined threshold is applied to the drive sleeve 30. In this way, a dose correction can be conducted even if the drive sleeve 30 is rotatably secured to the housing 20 by means of the ratchet member 32.

Displacement of the drive sleeve 30 in distal direction 1 disengages the ratchet member 32 from the first tooth profile 21. Consequently, when the drive sleeve 30 is in the distal dose dispensing position it is free to rotate in dose decrementing direction 6 under the effect of the helical spring element 43.

As further illustrated in FIG. 4, the piston rod 160 axially extends through a central and longitudinally extending bore 34 of the drive sleeve 30. The drive sleeve 30 may therefore also act as a linear guide for the piston rod 160.

Figure 13:
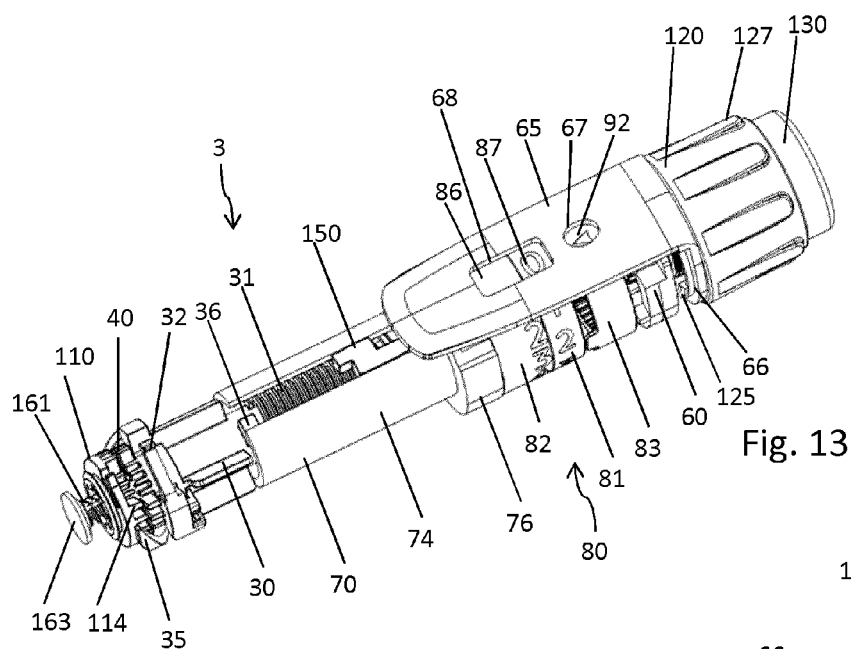
FIG. 13 shows an isolated and perspective illustration of the drive mechanism.
Figures 15, 16:
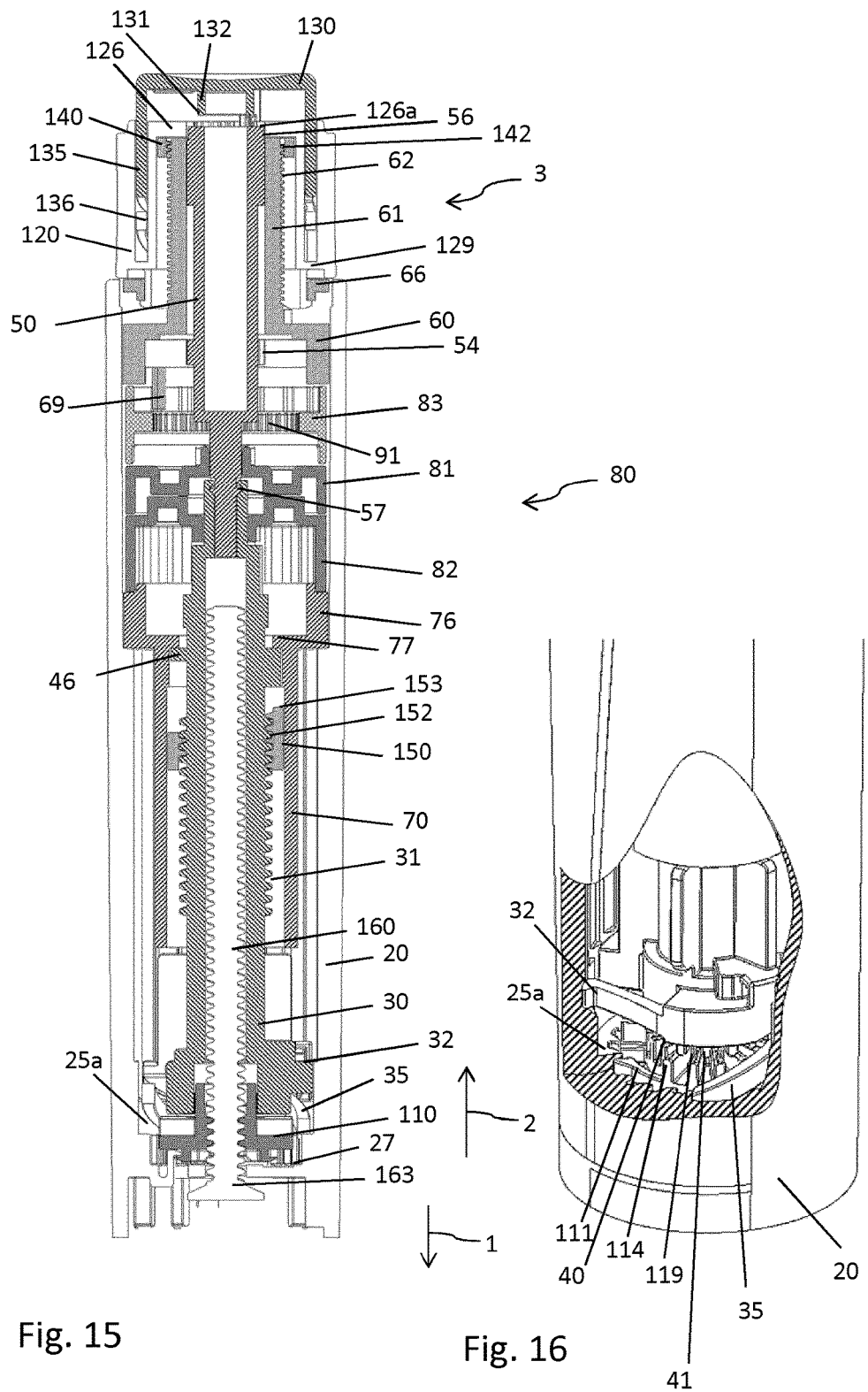
FIG. 16 shows a partially cut view through a distal end of the drive mechanism.

As further illustrated in FIGS. 13 and 16 the drive sleeve 30 comprises at least one retention spring element 35 at its distal end that is operable to axially engage and to axially abut against a radially inwardly extending flange 25*a* of the housing 20. In this way, the drive sleeve 30 is kept in the proximal dose setting position per default. A distally directed displacement of the drive sleeve 30 may therefore act against said at least one retention spring element 35. Bringing and keeping the drive sleeve 30 into the distal dose dispensing position therefore requires to constantly apply a respective thrust or pressure in distal direction 1 to the drive sleeve 30.

Figure 5:
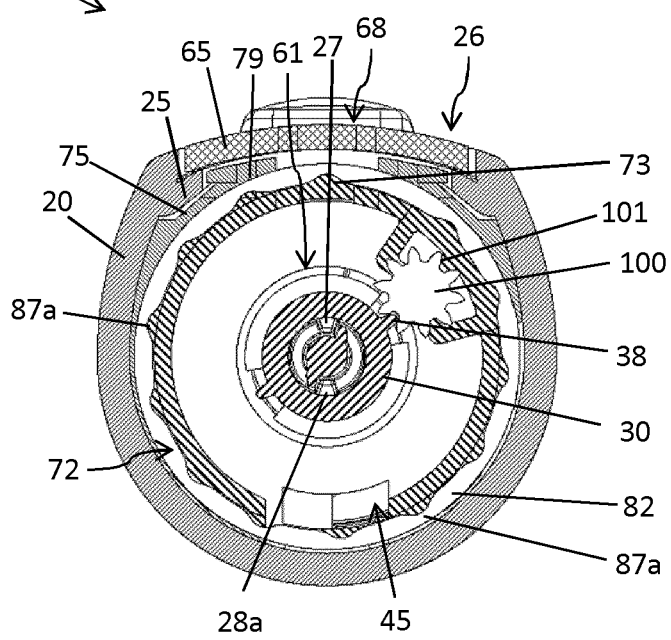
FIG. 5 shows a cross-section through the device along C-C according to FIG. 1.

A distally directed displacement of the drive sleeve 30 is limited by an axial abutment with a drive wheel 110 that is axially fixed to the housing 20 as illustrated in the cross-section according to FIG. 12. The drive wheel 110 is rotatably supported relative to the housing 20. In particular, the housing 20 comprises a radially inwardly extending guiding portion 27 featuring a central orifice 28 through which the threaded piston rod 160 extends. The piston rod 160 as further illustrated in FIG. 4 comprises two diametrically oppositely located radially inwardly and axially extending grooves 162 that engage with a correspondingly shaped radially inwardly extending protrusion 28a of the guiding portion 27 as indicated in FIG. 5.

The drive wheel 110 is axially fixed to the housing 20 by means of a positive engagement with a radially inwardly extending fixing member 29 having a radially inwardly extending latch portion to engage with a correspondingly shaped fastening or latch element 116 distally and radially outwardly extending from a distal flange portion 118 of the drive wheel 110. As indicated in FIG. 12, the housing's fixing member 29 is axially constrained between the latch element 116, its radially outwardly extending protrusion 117 and the radially outwardly extending flange portion 118 of the drive wheel 110. In this way, the drive wheel 110 is axially constrained and axially fixed to the housing 20 but may rotate with relative to the housing 20 with the longitudinal or central axis 4 as an axis of rotation.

Figure 11:
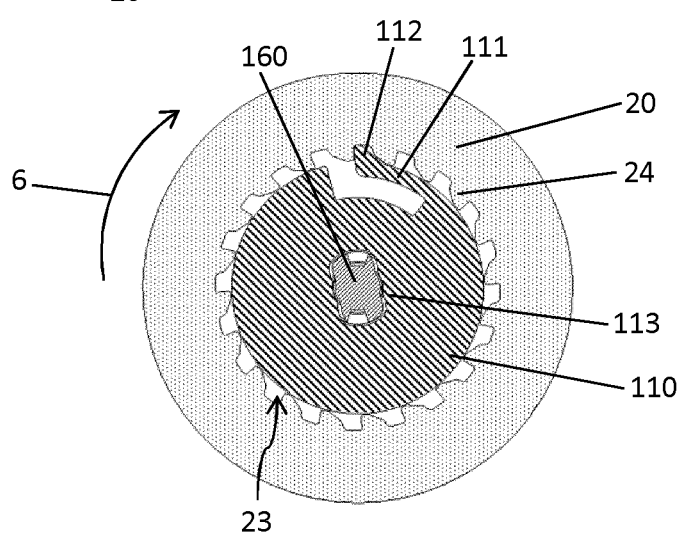
FIG. 11 shows a cross-section along J-J according to FIG. 1.

The mutual engagement of the drive wheel 110 with the fixing member 29 of the housing 20 however allows for a free rotation of the drive wheel 110 at least in a dose decrementing direction 6, as indicated in FIG. 11. As shown there, the drive wheel 110 comprises a circumferentially extending resiliently deformable interlocking member 111 featuring a radially outwardly extending ratchet tooth or protrusion 112 to engage with a second toothed profile 23 of the housing 20. The second toothed profile 23 comprises numerous ratchet teeth 24 radially inwardly protruding from an inward facing sidewall portion of the housing 20. By means of the mutual engagement of the drive wheel's 110 interlocking member 111 with the second toothed profile 23, only a unidirectional rotation of the drive wheel 110, namely in dose decrementing direction 6 is allowed if a respective torque acts on the drive wheel 110.

The ratchet tooth 112 of the interlocking member 111 as well as the shape and design of the various ratchet teeth 24 are designed such, that a dose incrementing rotation of the drive wheel 110 relative to the housing 20 is strictly blocked. In this way, a proximally directed displacement of the piston rod 160 relative to the housing 20 can be effectively prevented.

As it is further indicated in FIG. 12, the piston rod 160 comprises an outer threaded portion 161 threadedly engaged with a correspondingly shaped inner thread 115 of the drive wheel 110. Hence, the drive wheel 110 comprises a central orifice 113 to threadedly engage with the threaded portion 161 of the piston rod. By means of its groove 162 the piston rod 160 is rotatably locked to the housing 20 via the radially inwardly extending protrusions 28a thereof. If the drive wheel 110 rotates in dose decrementing direction 6 the axial fixing of the drive wheel 110 to the housing 20 and its threaded engagement with the piston rod 160 then leads to a distally directed but non-rotative and hence sliding movement of the piston rod 160.

Consequently, the radially widened pressure foot 163 located at a distal end of the piston rod 160 serves to exert distally directed pressure to the piston 14 for driving the same in distal direction 1 relative to the barrel of the cartridge 12. A rotation of the drive wheel 110 therefore directly transfers into a distally directed displacement of the piston rod 160.

Drive sleeve 30 and drive wheel 110 can be selectively coupled and decoupled to transfer angular momentum therebetween. The drive wheel 110 comprises a crown wheel 114 facing in proximal direction to engage with a correspondingly shaped crown wheel 40 of the drive sleeve 30 provided on a distal end of the drive sleeve 30. By means of displacing the drive sleeve 30 in distal direction 1, hence into its distal dose dispensing position, mutually corresponding crown wheels 40, 114 of drive sleeve 30 and drive wheel 110 mutually engage in a torque transferring way. In this way, a dose decrementing rotation 6 of the drive sleeve 30 can be directly transferred into a respective dose decrementing rotation of the drive wheel 110.

The axial dimensions of mutually corresponding teeth 41, 119 of the drive sleeve's 30 crown wheel 40 and the drive wheel's 110 crown wheel 114 is designed such, that respective crown wheels 40, 114 already engage and rotatably lock even before the drive sleeve 30 reaches the distal dose dispensing position. During a distally directed dose dispensing displacement of the drive sleeve 30 the crown wheels 40, 114 mutually engage before the ratchet member 32 of the drive sleeve 30 disengages from the first toothed profile 21 of the housing 20. In this way, a rather slip-free alternative rotational engagement and rotational disengagement of the drive sleeve 30 with the drive wheel 110 and housing 20 can be achieved.

Figure 17:
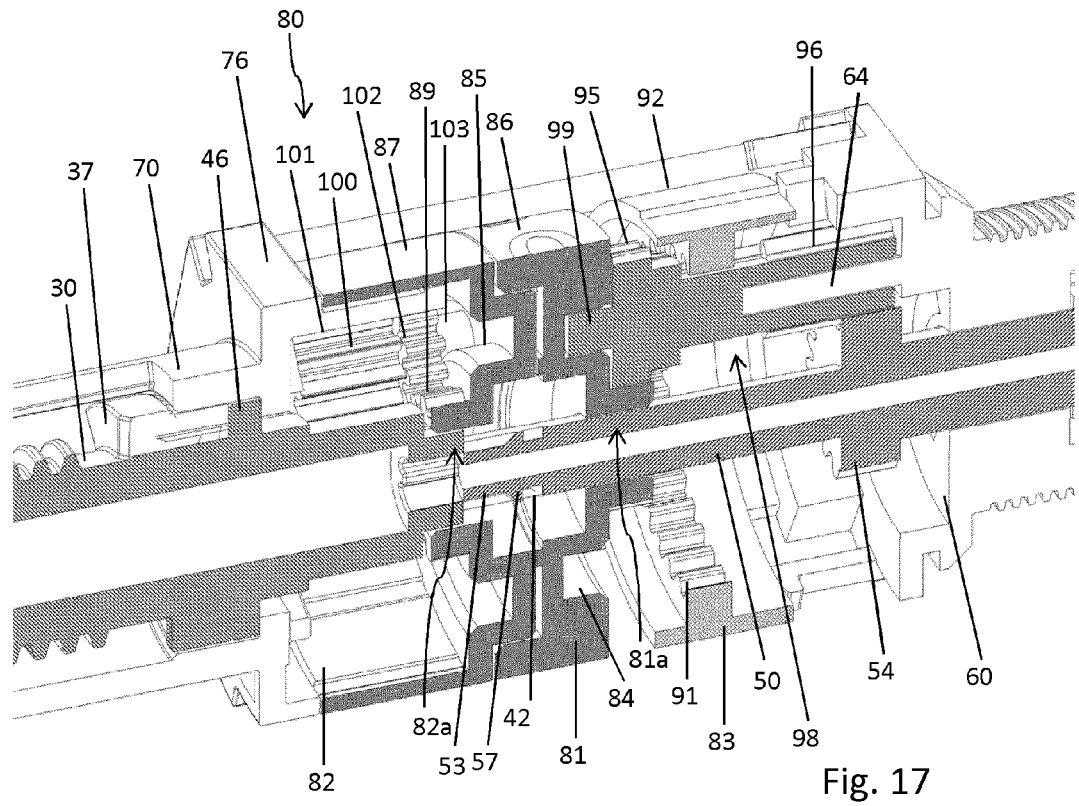
FIG. 17 shows a perspective and longitudinally cut view of the display assembly.

As in detail illustrated in FIG. 17, a proximal end of the drive sleeve 30 is rigidly connected and fixed to a distal end portion of a dose setting sleeve 50, which in proximal direction 2 extends into or almost through a proximal threaded shaft portion 61 of a proximal base member 60. The dose setting sleeve 50 comprises at least one radially outwardly extending protrusion 57 to engage with a correspondingly shaped indentation or with a respective latch element 42 of the drive sleeve 30. In this way, the dose setting sleeve 50 and the drive sleeve 30 can be rigidly attached in axial direction to transfer a distally directed thrust from the dose setting sleeve 50 towards the drive sleeve 30.

Additionally and as shown in FIG. 6, dose setting sleeve 50 and drive sleeve 30 are also rotatably engaged by mutually corresponding connecting portions. Here, the drive sleeve 30 comprises a non-circular shaped receptacle 39a to receive a correspondingly shaped connector 53 of the dose setting sleeve 50. In this way also a rotation of the dose setting sleeve 50 unalterably transfers into a respective rotation of the drive sleeve 30.

Figure 14:
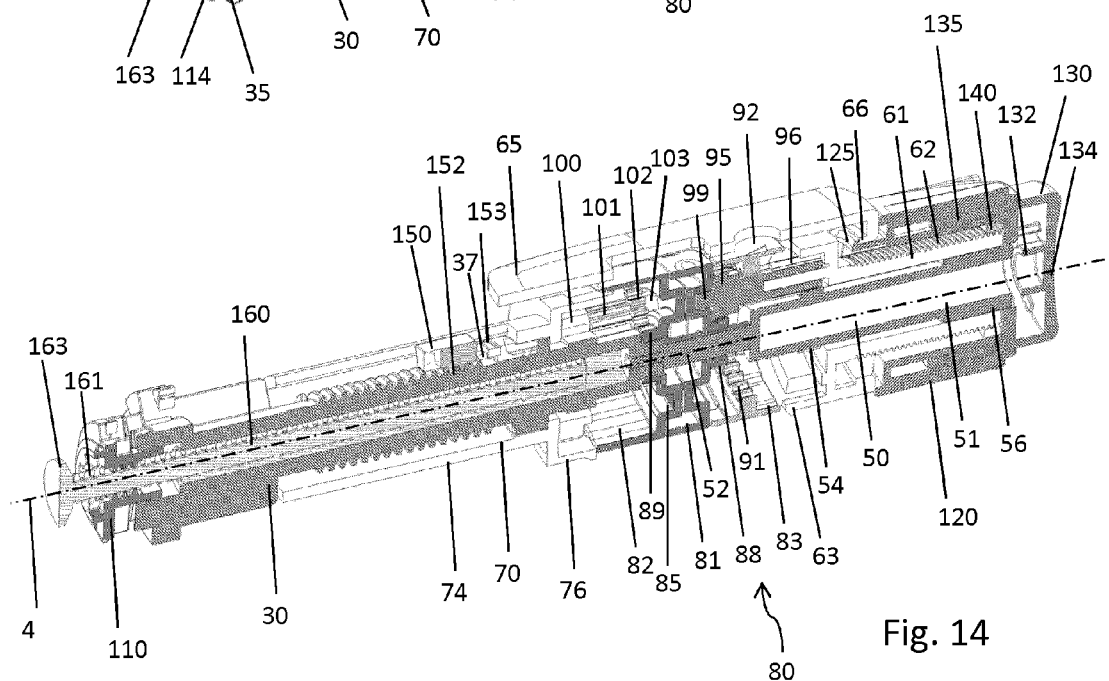
FIG. 14 shows the drive mechanism in a perspective illustration in a longitudinal cross section, FIG. 15 provides another longitudinal cross section through the drive mechanism.

The drive mechanism 3 further comprises a display assembly 80 which is illustrated in detail in FIGS. 14 and 17. The display assembly 80 comprises a first dose indicating member 81 and a second dose indicating member 82. The dose indicating members 81, 82 comprise a disc-like or sleeve-like shape and both comprise annular display surfaces 86, 87 to visually display variable dose sizes through a window 68 of a cover portion 65 or through a sidewall portion of the housing 20.

The first dose indicating member 81 comprises a first display surface 86 while the second dose indicating member 82 comprises a second annular display surface 87. While the first display surface 86 represents single units of the medicament to be dispensed and therefore comprises numerals from 0-9 the second dose indicating member 82, in particular its display surface 87 comprises numerals from 0, 1, 2, and so on thereby representing decades or tens, such like 10, 20 so on. If the drive mechanism 3 is for instance adapted to set and to inject a maximum dose of insulin of e.g. 120 IU, the numbers present on the second annular display surface 87 range from 1-12.

The two dose indicating members 81, 82 are both rotatably arranged on the longitudinal axis 4 and may be rotated in a dose incrementing direction 5 during dose setting and in an opposite direction, hence in dose decrementing direction 6 during dose dispensing. Accordingly, the numbers showing up in the window 68 either constantly increase or constantly decrease during dose setting and dose dispensing.

Moreover, the first dose indicating member 81 comprises a central orifice 81a and the second dose indicating member 82 comprises a second central orifice 82a. Said orifices 81a, 82a axially flush and are adapted to receive the dose setting sleeve 50 and/or the drive sleeve 30 as becomes apparent from the sketch of FIG. 17. Even though the assembly of dose setting sleeve 50 and drive sleeve 30 extends through both dose indicating members 81, 82, there is only an indirect transfer of angular momentum between dose setting sleeve 50, drive sleeve 30 and the two dose indicating members 81, 82.

In particular, the first and second dose indicating members 81, 82 are axially fixed relative to the housing 20 and/or relative to the proximal base member 60 and/or to the distal base member 70 as for instance illustrated in FIG. 17. In contrast to that, the assembly of drive sleeve 30 and dose setting sleeve 50 is axially displaceable relative to both dose indicating members 81, 82 for switching the drive mechanism 3 between the dose setting mode and the dose dispensing mode.

Figure 7:
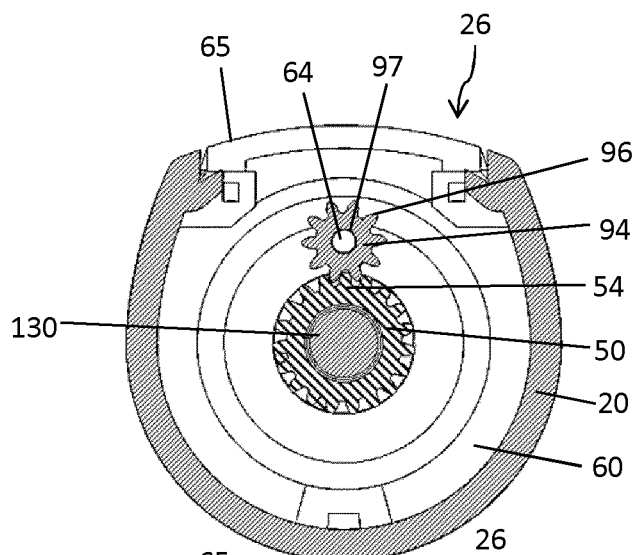
FIG. 7 shows a cross-section along E-E according to FIG. 1.
Figure 8:
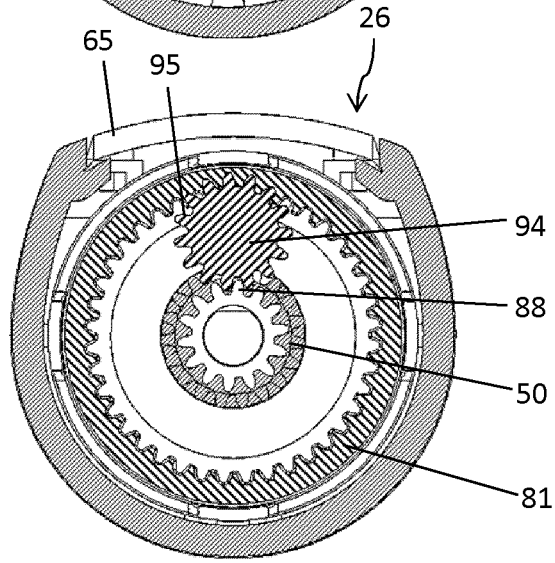
FIG. 8 shows a cross-section along F-F according to FIG. 1.

In order to transfer a driving torque between dose setting sleeve 50, drive sleeve 30 and at least one of first and second dose indicating members 81, 82 there are provided first and second display wheels 94, 100. As indicated in FIGS. 17 and 7 the dose setting sleeve 50 comprises a first geared portion 54 that meshes with a correspondingly shaped proximally located geared section 96 of the first display wheel 94. Said display wheel 94 further comprises a proximally located pocket hole or receptacle 97 to receive a distally and axially extending pin or bearing 64 of the proximal base member 60.

Distally offset from the proximal geared section 96 the first display wheel 94 further comprises a distal geared section 95 that meshes with a central gear 88 of the first dose indicating member 81. In this way, a dose incrementing or dose decrementing rotation of the dose setting sleeve 50 can be transferred into a respective rotation of the first dose indicating member 81. The first dose indicating member 81 and the second dose indicating member 82 are only indirectly rotatably engaged via the drive sleeve 30 and the dose setting sleeve 50.

Figure 19:
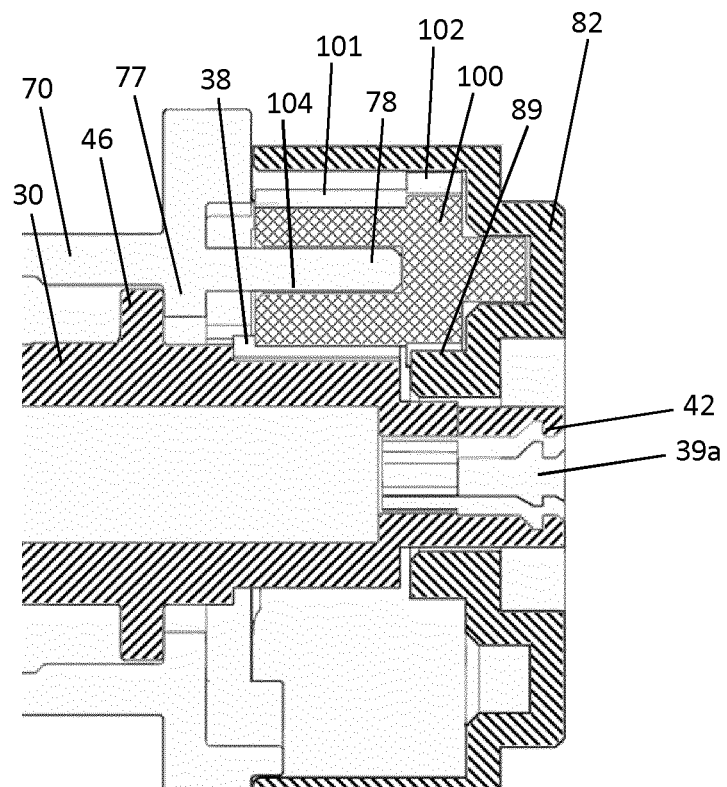
FIG. 19 shows a longitudinal and enlarged cross section through a proximal portion of the display assembly.

Hence, the second dose indicating member 82 is rotatably engaged with the drive sleeve 30 by means of the second display wheel 100. Similar as the first display wheel 94 also the second display wheel 100 is located radially offset from the longitudinal central axis 4 but is located radially inward compared to the display surface 86, 87 of first and/or second dose indicating members 81, 82. Also the second display wheel 100 is rotatably supported on an axially but proximally extending pin or bearing 78 of the distal base member 70 as indicated in FIG. 19. A distally located geared section 101 of the second display wheel 100 meshes with a radially outwardly extending tappet 38 of the drive sleeve 30 as indicated in FIG. 5. In this way, a continuous rotation of the drive sleeve 30 transfers to a discrete and stepwise rotation of the second display wheel 100.

The second display wheel 100 further comprises a proximally located geared section 102 that meshes with a central gear 89 of the second dose indicating member 82.

In the present embodiment according to FIG. 5 the drive sleeve 30 comprises two oppositely located tappets 38. Accordingly, during a complete revolution of the drive sleeve 30, the second dose indicating member 82 is subject to two consecutive discrete stepwise rotations.

By means of first and second display wheels 94, 100 extending parallel to the longitudinal axis 4 and hence parallel to the drive sleeve 30 and dose setting sleeve 50, the dose setting sleeve 50 and the drive sleeve 30 always rotate in the same sense of rotation as the first and second dose indicating members 81, 82.

Moreover and as illustrated in FIG. 17 the first dose indicating member 81 comprises a first annular groove 84 that is open towards the proximal direction 2 while the second dose indicating member 82 comprises a second annular groove 85 that is open towards the distal direction. Both annular grooves 84, 85 are particularly adapted to receive a pin 99, 103 of first and second display wheels 94, 100, respectively. In this way, the distal end of the first display wheel 94 can be radially constrained by the first dose indicating member 81 while a proximal end of the second display wheel 100 can be radially confined by the second dose indicating member 82.

Figure 18:
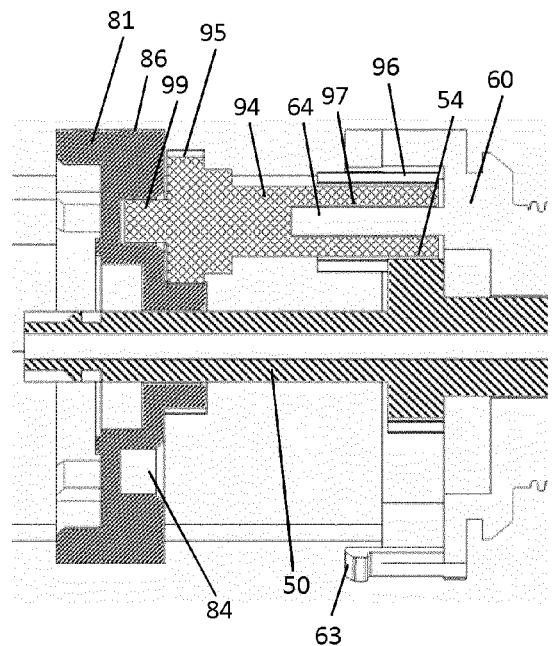
FIG. 18 shows a longitudinal and magnified cross section through a proximal portion of the display assembly.

Since the two dose indicating members 81, 82 directly abut in axial direction the first as well as the second dose indicating member 81, 82 can be axially constrained and axially supported by their respective first and second display wheels 94, 100. As indicated in FIG. 18, the first display wheel 94 with its pocket hole 97 axially abuts with the distally extending bearing 64 of the proximally located base member 60. The oppositely located pin 99 is in axial engagement with the annular groove 84 of the first dose indicating member 81. In a corresponding way also the pocket hole 104 of the second display wheel 100 receives the proximally extending bearing 78 of the distal base member 70 thereby supporting the second dose indicating member 82 by means of an axial abutment of its proximal pin 103 with the annular groove 85 of the second dose indicating member 82.

In this way, the first dose indicating member 81 can be axially supported in proximal direction 2 by the first display wheel 94 while the second dose indicating member 82 can be axially supported in distal direction 1 by means of the second display wheel 100. When interconnecting the two base members 60, 70 the first and second dose indicating members 81, 82 mutually abut and are therefore axially constrained and axially fixed relative to first and/or second base members 60, 70. In embodiments, wherein the first and second base members are fixedly attached to the housing 20, first and second dose indicating members 81, 82 are also axially constrained and fixed to the housing 20.

The first and the second display wheels 94, 100 remain permanently engaged with the dose setting sleeve 50 and the drive sleeve 30, respectively. Hence, the axial elongation of the respective geared sections 96, 101 of first and second display wheel 94, 100 allows for a distally directed displacement of drive sleeve 30 and dose setting sleeve 50 for switching the drive mechanism 3 between dose dispensing mode and dose setting mode.

Having a proximal base member 60 and a distal base member 70 allows for an almost complete assembly of the drive mechanism 3 before the drive mechanism 3 in its entirety is inserted into and fixed to the housing 20. As further illustrated in FIG. 15 the distal base member 70 comprises a radially widened receptacle portion 76 at its proximal end to receive and to support the display assembly 80.

Additionally, the display assembly 80 further comprises a third dose indicating member 83 that is axially offset from first and second dose indicating members 81, 82. In the present embodiment as illustrated in FIGS. 13 and 17 the third dose indicating member 83 also comprises an annular shape and features a third display surface 92 that is discernable through another window 67 of the cover portion 65 of the proximal base member 60. The third display surface 92 features a symbol or a color to visually indicate to the user whether the device 10 is in an idle state and is ready for setting of a dose or whether a dose setting or dose dispensing process is actually in progress.

Figure 9:
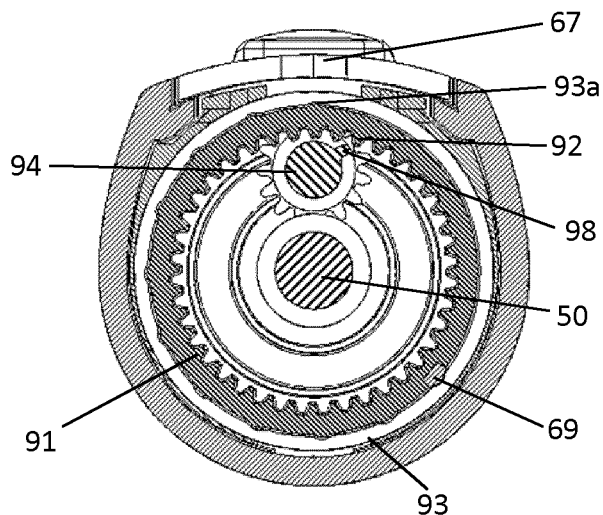
FIG. 9 shows a cross-section along G-G according to FIG. 1.

The third dose indicating member 83 comprises a geared rim 91 on its inside facing sidewall portion that is adapted to engage with a radially outwardly extending tappet 98 of the first display wheel 94 as indicated in FIG. 9. The tappet 98 is located axially between the distal geared section 95 and the proximal geared section 96 of the first display wheel.

The second as well as the third display wheel 82, 83 further comprise or interact with a retaining structure for keeping the respective dose indicating member 82, 83 in a particular rotational position when the tappet 98 of the first display wheel 94 and hence the tappet 38 of the drive sleeve 30 is actually disengaged from the retaining structure 93 or from the geared section 101 of the display wheel 100. As illustrated in FIGS. 1 and 9 the proximal base member 60 comprises a distally extending retaining member 69 of pin-like shape and featuring a radially outwardly extending bulged portion to engage with a correspondingly shaped recess 93a of the third dose indicating member's 83 retaining structure 93.

The circumferential distance of adjacent recesses 93a corresponds to the mutual engagement of the geared rim 91 and the tappet 98. In this way, discrete and stepwise rotation of the third dose indicating member 83 always starts and ends with a mutual engagement of the retaining member 69 with the retaining structure 93. In this way, the third dose indicating member 83 can be rotatably secured to the base member 60 and hence to the housing 20 if the tappet 98 even when the first display wheel 94 is disengaged from the geared rim 91 of the third dose indicating member 83.

In a similar way also the second dose indicating member 82 can be rotatably secured to the distal base member 70. As indicated in FIGS. 5 and 6, the base member 70 comprises a radially outwardly extending annular shaped retaining structure 72 featuring various radially outwardly but circumferentially spaced protrusions 73. As shown in FIGS. 5 and 6, the second dose indicating member 82 comprises a correspondingly shaped inside facing recessed structure with numerous recesses 87a that correspond and engage with the radially outwardly extending protrusion 73 of the base member 70. Also here, the mutually corresponding recesses 87a and protrusions 73 serve to provide a stepwise and consecutive securing or engagement of the second dose indicating member 82 with the base member 70.

From the sketches of FIGS. 5, 7 and 14 also the mutual assembly of the proximal base member 60 with the housing 20 becomes apparent. The housing 20 comprises a longitudinally extending slot or recess 26 at its proximal end to receive the cover portion 65 of the proximal base member 60. At circumferential side edges of the recess 26 the housing 20 comprises radially inwardly located prongs 25 extending from opposite sides at least partially into the recess 26 in tangential or circumferential direction. Here, the prongs 25 provide a radial support structure for the cover portion 65. Additionally, the prongs 25 extend radially inwardly from the inner sidewall of the housing 20 and may therefore engage with a correspondingly shaped recess 75 of an arc-shaped fixing portion 79 of the distal base member 70.

By means of this positive engagement the proximal as well as the distal base members 60, 70 can be rotatably fixed to the housing 20. Moreover, as illustrated in FIG. 14 the proximal base member 60 comprises at least one distally extending and radially deformable fastening element 63 by way of which the proximal base member 60 can be axially fixed to the housing 20. In particular, the proximal base member 60 can be clipped to the housing 20 while the distal base member 70 may axially abut against a radially stepped or recessed portion of the housing 20.

As shown in detail in FIGS. 14 and 15 the proximal base member 60 comprises a proximal shaft portion 61 featuring an outer thread 62. Additionally and radially offset from said shaft portion 62, the proximal base member 60 comprises a radially inwardly extending flange portion 66 adapted to engage with a fastening element 125 of a dose setting member 120. As indicated in FIG. 14, the sleeve-shaped dose setting member 120 comprises a latch-like radially resiliently deformable fastening element 125 to engage with the indentation formed by the radially inwardly extending flange portion 66 of the proximal base member 60. In this way, the dose setting member 120 can be axially fixed to the base member and may freely rotate relative to the base member.

Additionally, there is provided a cup-shaped dose dispensing member 130. Said dose dispensing member 130 may be permanently rotatably engaged with the sleeve like dose setting member 120 as becomes apparent from the cross-section according to FIG. 3. The dose dispensing member 130 acting as a dose button comprises an axially extending shaft portion 132 extending towards a proximal end of a proximal sleeve portion 51 of the dose setting sleeve 50 extending through the hollow proximal shaft portion 61 of the proximal base member 60.

Figure 3:
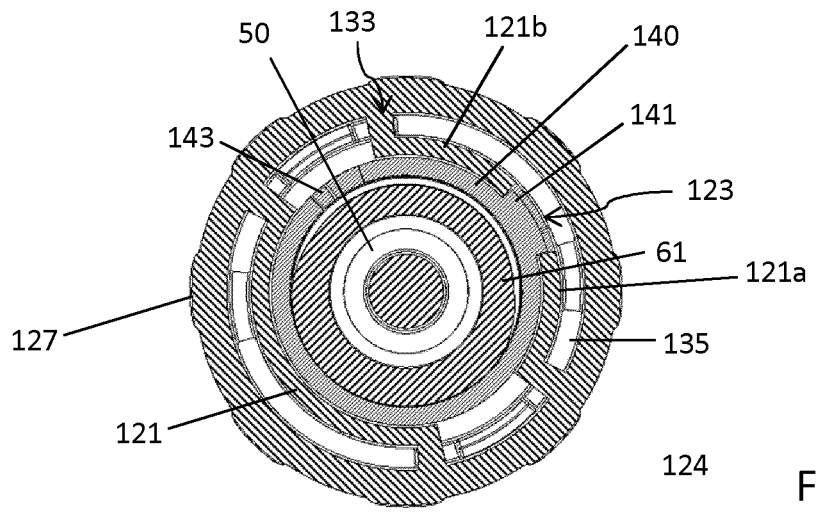
FIG. 3 shows a cross-section along A-A according to FIG. 1.

The dose setting member 120 comprises an annular cross-section featuring various grip structures 127 at its outer surface. The dose setting member 120 further comprises various radially inwardly extending protrusions 124 extending into circumferentially extending arched portions 121, 121a, 121b as illustrated in FIG. 3. Here, the protrusions 124 may act as bridging portions for integrally connecting the inner arched portion 121 with the outer sleeve portion of the dose setting member 120. Between arched portions 121a, 121b there is formed an axially extending slot or recess 123 to receive a radially outwardly extending protrusion 141 of a last dose limiting member 140.

As indicated in FIGS. 3 and 14 said last dose limiting member 140 is radially sandwiched between the proximal base member 60, in particular between its proximal shaft portion 61 and the dose setting member 120. The last dose limiting member 140 comprises an inner thread 142 threadedly engaged with the outer thread 62 of the proximal base member 60. In this way, the annular shaped last dose limiting member 140 is subject to a rotation relative to the base member 60 when the dose setting member 120 is dialed either in a dose incrementing direction 5 or dose decrementing direction 6s.

Due to the axially elongating recess 123 of the dose setting member 120 the last dose limiting member 140 is allowed to travel in axial direction as the dose setting member 120 is rotated.

Figure 20:
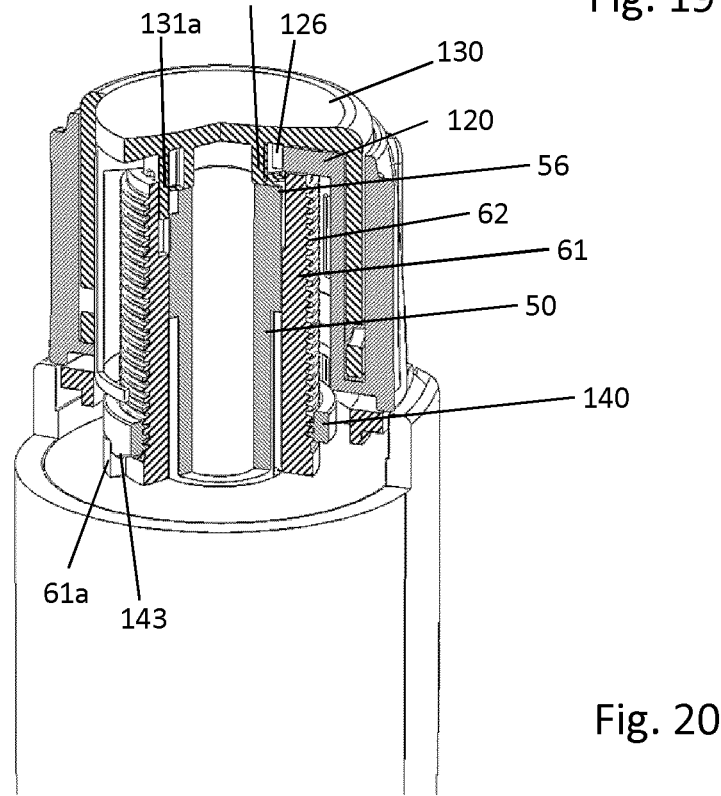
FIG. 20 shows a partially cut and perspective view of the proximal end of the drug delivery device with a depressed dose dispensing member.

The last dose limiting member 140 further comprises a radial stop 143 to engage with a correspondingly shaped radial stop 61a of the base member 60 when reaching an end-of-content configuration which is illustrated in FIG. 20.

As illustrated in detail in FIG. 15, the dose dispensing member 130 extends with a sidewall portion 135 between the inner arched portions 121, 121a, 121b of the dose setting member 120 and the outer sidewall portion 128 of the dose setting member 120. Moreover, and as illustrated in FIG. 15 the dose dispensing member 130 comprises at least one or several axially extending spring elements 136 to abut against a bottom portion 129 of the dose setting member 120. Said bottom portion 129 may radially extends between and may connect the arched portions 121 with the radially outwardly located sidewall portion 128 of the dose setting member 120.

In this way the dose dispensing member 130 can be axially displaced in distal direction 1 relative to the dose setting member 120 against the action of the at least one spring element 136. This spring element 136 is of particular use to bring and to transfer the dose dispensing member 130 into a proximal dose setting configuration as for instance illustrated in FIG. 15.

For transferring the drive mechanism 3 from the dose setting mode into the dose dispensing mode a user simply depresses the dose dispensing member 130 in distal direction 1. Then, the shaft portion 132 thereof axially abuts with a proximal end of the dose setting sleeve 50 thereby displacing the dose setting sleeve 50 in distal direction 1. Since the dose setting sleeve 50 is axially rigidly connected with the drive sleeve 30 also the drive sleeve 30 experiences a respective distally directed displacement until it reaches the distal dose dispensing configuration, in which the drive sleeve 30 is liberated from the housing 20 and in which the drive sleeve 30 is free to rotate under the action of the helical spring element 43.

Moreover, by displacing the dose dispensing member 130 in distal direction 1 a geared portion 131 of the axially extending shaft portion 132 of said dose dispensing member 130 is adapted to rotatably lock to the proximal base member 60, thereby inhibiting a potential rotation of the dose dispensing member 130 relative to the base member 60 or relative to the housing 20.

Since the dose dispensing member 130 is permanently rotatably locked to the dose setting member 120 by the radially inwardly extending protrusions 124 extending through respective recesses or slots 133 of the dose dispensing member 130 also the dose setting member 120 is rotatably locked to the base member 60 when the dose setting member 120 is in its distal dose dispensing position. Due to the rotational interlocking of the dose setting member 120 relative to the base member 60 the dose setting member 120 cannot rotate during a dose dispensing procedure. In this way also the last dose limiting member 140 cannot be rotated or axially displaced during a dose dispensing procedure.

Moreover, as indicated in FIG. 15 the dose setting member 120 comprises a radially inwardly extending flange portion 126 at its proximal end featuring a central through opening with a radially inwardly extending geared structure 126a. Said geared structure 126a is rotatably engaged with a correspondingly shaped geared portion 56 of the proximal sleeve portion 51 of the dose setting sleeve 50. When located in proximal dose setting position the dose setting sleeve 50 is hence rotatably locked or rotatably engaged with the dose setting member 120. A rotation of the dose setting member 120 relative to the base member 60 therefore leads to a respective rotation of the dose setting sleeve 50 and hence to a respective rotation of the drive sleeve 30.

By displacing the dose dispensing member 130 in distal direction 1 and by correspondingly displacing the dose setting sleeve 50 in its distal dose dispensing position the dose setting sleeve 50 is operably disengaged from the dose setting member 120. At the same time, or even prior to the disengagement of dose setting sleeve 50 and dose setting member 120 the dose dispensing member 130 rotatably locks to the proximal base member 60.

In this way the dose setting member 120 is only rotatable when the drive mechanism 3 is in dose setting mode. Due to the decoupling of the dose setting sleeve 50 from the dose setting member 120 during a dose dispensing the axial position of the last dose limiting member 140 reflects the sum of doses consecutively set and dispensed by the drive mechanism.

In the following setting of a dose if described.

For setting of a dose a user simply dials the dose setting member 120 in dose incrementing direction 5. Due to its rotational engagement with the dose setting sleeve 50 also said dose setting sleeve 50 together with the drive sleeve 30 are rotated accordingly against the action of the helical spring element 43. Said rotational displacement is secured by the drive sleeve's 30 ratchet member 32. Here, the ratchet member 32 provides an audible feedback to the user as it meshes along consecutive radially inwardly extending teeth 22 of the first toothed profile 21 of the housing 20. Since the ratchet member 32 is resiliently deformable it is operable to generate a click sound when rotated relative to the teeth 22 of the first toothed profile 21. Additionally, at least the first dose indicating member 81 as well as the third dose indicating member 83 are rotated in a dose incrementing way, thereby illustrating to the user the size of the dose actually set.

Figure 10:
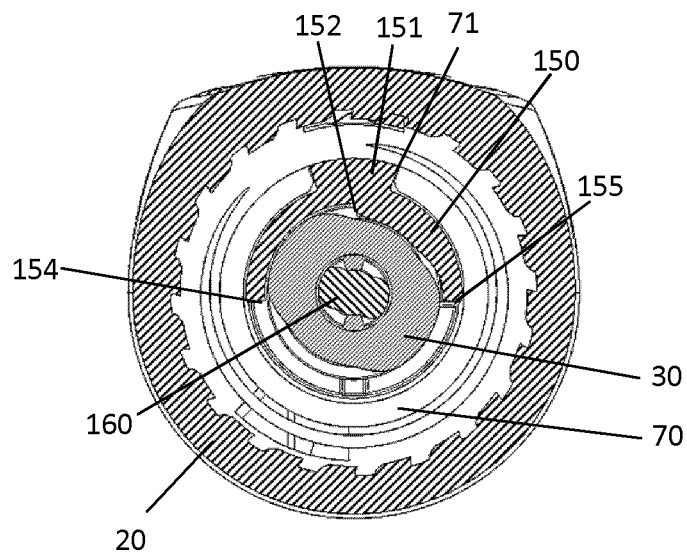
FIG. 10 shows a cross-section through the device along H-H according to FIG. 1

Moreover, and as becomes apparent from FIGS. 10 and 15, there is a provided a single dose limiting member 150 disposed radially between the drive sleeve 30 and the distal base member 70. Here, the arc-shaped or semicircular-shaped single dose limiting member 150 comprises a radially outwardly extending protrusion 151 engaged with a correspondingly radially outwardly extending and axially elongated recess 71 of a distal sleeve portion 74 of the base member 70. In this way, the single dose limiting member 150 is rotatably locked to the stationary base member 70 and may only slide along the axially extending groove or recess 71 thereof during a dose incrementing or a dose decrementing rotation 5, 6 of the drive sleeve 30.

Additionally and as illustrated in FIG. 15 the drive sleeve comprises an outer threaded portion 31 engaged with an inner thread 152 of the single dose limiting member 150. It is due to the keyed or splined engagement of the single dose limiting member 150 with the distal base member 70 and due to the threaded engagement of the single dose limiting member 150 with the drive sleeve 30 that a rotation of the drive sleeve 30 transfers to an axial displacement of the single dose limiting member 150. The single dose limiting member 150 comprises at least one radial stop 154, 155, e.g. at its circumferential end to engage with a correspondingly shaped radial stop 36 of the drive sleeve 30, e.g. located near a distal end of its threaded portion 31. As the drive sleeve 30 is dialled and rotated in dose incrementing direction 5 the single dose limiting member 150 may advance in distal direction 1 until it engages with the distal stop 36 of the drive sleeve 30.

When mutually corresponding radial stop faces 155 and radial stop 36 get in direct abutment a further rotation of the drive sleeve 30 is effectively blocked due to the splined or keyed engagement of the single dose limiting member 150 with the distal base member 70. The axial position of the stop 36 as well as the lead of the threaded engagement of the single dose limiting member 150 and the drive sleeve 30 is adapted such that such a blocking configuration correlates to a maximum allowable dose size, of e.g. 120 IU of insulin.

The oppositely located radial stop 154 of the single dose limiting member 150 may act as a zero dose stop adapted to engage with another radial but proximally located stop 37 of the drive sleeve 30. Mutual engagement of the radial stop 154 of the single dose limiting member 150 with the proximally located stop 37 of the drive sleeve 30 effectively inhibits that a user may set a negative dose.

Additionally, the single dose limiting member 150 further comprises a resiliently deformable clicking member 153 that may at least occasionally audibly engage with the stop 37 of the drive sleeve 30 as the single dose limiting member 150 approaches a zero dose configuration, in particular when a dose dispensing procedure terminates. In this way, an audible feedback can be provided to a user that the drive mechanism 3 returns into an initial state. The clicking member is typically axially deformable and may therefore audibly engage the stop 37 drive sleeve 30 radially outwardly extending therefrom.

Since the single dose limiting member 150 is permanently threadedly engaged with the drive sleeve 30 it moves forth and back as the drive sleeve 30 is rotated in dose incrementing direction 5 during dose setting and as the drive sleeve 30 is rotated in the opposite, dose decrementing direction 6 during dose dispensing or dose correction.

After a dose of intended size has been set the drive mechanism 3 and hence the drug delivery device 10 is ready for dispensing of said dose.

In the following dispensing of a dose is described

The dispensing procedure is started by depressing the dose dispensing member 130 in distal direction 1. Then, the dose dispensing member 130 rotatably locks to the proximal base member 60 and therefore also locks a rotation of the dose setting member 120 relative to the proximal base member 60. As shown in FIG. 20 the dose dispensing member 130 comprises a distally extending pin 131a to engage with a correspondingly shaped recessed structure (not illustrated) of the proximal base member 60. When depressing the dose dispensing member 130 in distal direction it rotatably locks to the proximal base member 60 by means of the pin 131a, thereby also impeding a further rotation of dose setting member 120 when the device 10 is in dose dispensing mode. By means of this kind of interlocking misuse of the device, hence dialing of the dose setting member during dose dispensing is effectively prevented.

The axial position of the last dose limiting member 140 is then fixed at least during the duration of the dose dispensing procedure. Additionally, the distally extending shaft portion 132 axially abuts with the dose setting sleeve 50 and drives the dose setting sleeve 50 out of engagement from the dose setting member 120. Since the axial displacement of the dose setting sleeve 50 is directly and unalterably transferred to the drive sleeve 30 the drive sleeve 30 will engage with its crown wheel 40 with the correspondingly shaped crown wheel 114 of the drive wheel 110.

After or as soon as a torque transmitting coupling of drive sleeve 30 and drive wheel 110 is established the ratchet member 32, e.g. integrally formed with the drive sleeve 30, also disengages from the first toothed profile 21 of the housing 20, thereby liberating and releasing the rotation of the drive sleeve 30. Consequently, the drive sleeve 30 and hence the drive wheel 110 start to rotate in the dose decrementing direction 6 under the effect of the helical spring element 43 previously strained and biased during dose setting.

As already described, not only the piston rod 160 is driven in distal direction 1 by the revolutions of the drive wheel 110 but also the single dose limiting member 150 returns into its initial position until its radial stop 154 engages with a corresponding radial stop 37 of the drive sleeve. Additionally, the clicking element 153 audibly engages with the stop 37 of the drive sleeve in order to audibly indicate to a user that a dose dispensing procedure just terminated.

During the entire dose injection or dose dispensing process it is required that the user keeps the dose dispensing member 130 depressed against the action of the retention spring element 35 of the drive sleeve 30. When releasing the dose dispensing member 130 the drive sleeve 30 as well as the dose setting sleeve 50 interconnected therewith return into their proximal dose setting position which is e.g. characterized by a radially outwardly extending flange portion 46 of the drive sleeve 30 that axially abuts with a correspondingly shaped radially inwardly extending flange portion 77 of the distal base member 70 as illustrated for instance in FIG. 15. This proximally directed displacement of the drive sleeve 30 and the dose setting sleeve 50 also disengages the rotational interlock of the dose dispensing member 130 and the proximal base member 60. As a consequence, the dose setting member 120 may be repeatedly rotated for setting of a consecutive dose.

As it becomes further apparent from FIG. 11 a dose decrementing rotation of the drive wheel 110 during a dose dispensing procedure is typically accompanied by the interlocking member 111 meshing with the ratchet teeth 24 of the second toothed profile 23. Dose decrementing rotation of the drive wheel 110 is therefore accompanied with an audible feedback, e.g. in form of a clicking noise indicating to a user of the device 10 that a dose dispensing procedure is actually in progress.

Figure 21:
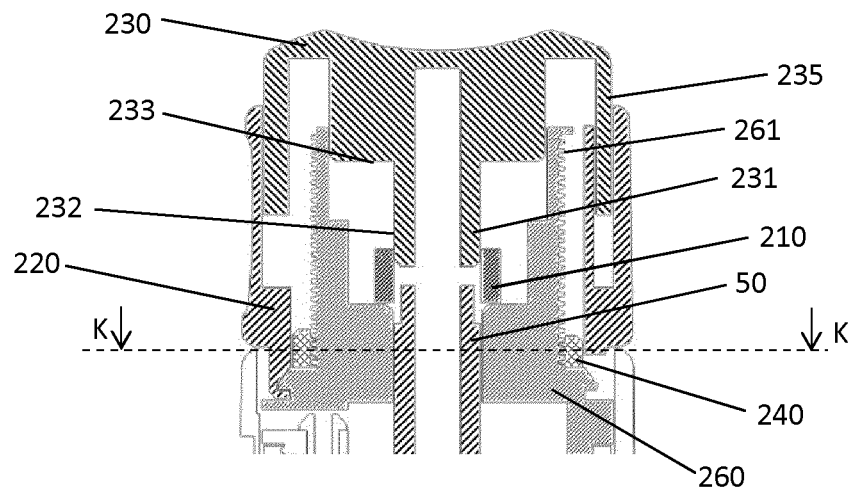
FIG. 21 shows an enlarged view of a proximal end of the drive mechanism according to an alternative embodiment and FIG. 22 shows a cross-section K-K through the embodiment according to FIG. 21.
Figure 22:
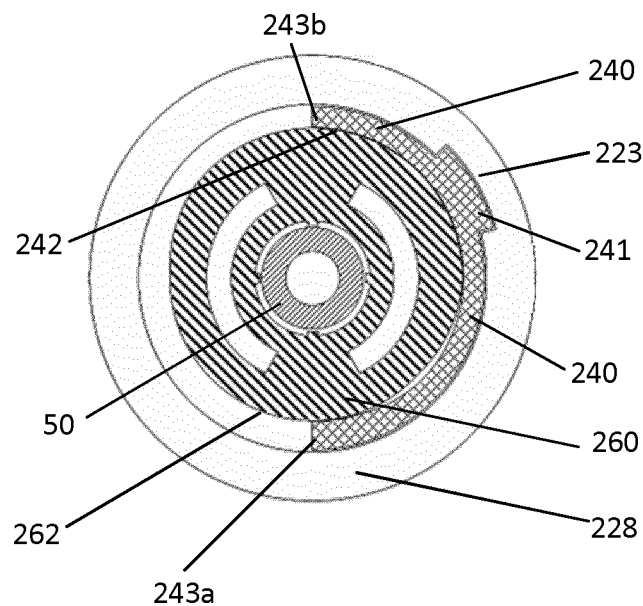

In FIGS. 21 and 22 an alternative embodiment is illustrated, wherein the last dose limiting member 240 only comprises a semi-circular, arched shape with oppositely located radial stop portions 243a, 243b to engage with correspondingly shaped radial stop portions of the proximal base member 260. Also here, the proximal base member 260 comprises a proximally extending shaft portion 261 featuring an outer thread 262 to engage with an inner thread 242 of the last dose limiting member 240. The dose setting member 220 comprises a recess 223 at its inside facing sidewall portion 228 to receive the radially outwardly extending protrusion 241 of the last dose limiting member 240.

Also here, the dose dispensing member 230 comprises a distally extending shaft portion 231 to apply distally directed thrust to the co-aligned dose setting sleeve 50. The sidewall portions 235 and 228 of the dose dispensing member 230 and the dose setting member 220 are rotatably engaged, e.g. by mutually corresponding radially extending protrusions and recesses, that are not particularly illustrated here. In this way also a permanent rotational interlock of dose setting member 220 and dose dispensing member 230 can be attained.

For rotatably securing or rotatably interlocking the dose dispensing member 230 to the base member 260 the dose dispensing member 230 comprises a stepped portion 233 that may either comprise a crown wheel or radially outwardly extending gears to rotatably lock to the proximal base member 260 when distally displaced in dose dispensing position.

Additionally, there is provided a sleeve-shape transfer element 210 that serves as a torque transmitting coupling member between the dose setting sleeve 50 and the shaft portion 232 of the dose dispensing member 230. In the embodiment according to FIGS. 20 and 21 a user induced rotation of the outer dose setting member 220 is first transferred to a respective rotation to the dose dispensing member 230 and is then transferred via the dose dispensing member 230 and its distally extending shaft portion 232 via the transfer element 210 to the dose setting sleeve 50. By distally displacing the dose dispensing member 230 for dose dispensing the dose setting sleeve 50 is advanced and pushed in distal direction so as to disengage from the geared transfer element 210.

LIST OF REFERENCE NUMERALS 1 distal direction
2 proximal direction
3 drive mechanism
4 longitudinal axis
5 dose incrementing direction
6 dose decrementing direction
10 drug delivery device
12 cartridge
13 cartridge holder
14 piston
16 needle assembly
17 injection needle
18 needle cap
19 protective cap
20 housing
21 toothed profile
22 ratchet tooth
23 toothed profile
24 ratchet tooth
25 prong
25a flange portion
26 recess
27 guiding portion
28 orifice
28a protrusion
29 fixing member
30 drive sleeve
31 threaded portion
32 ratchet member
33 catch portion
34 bore
35 spring element
36 stop
37 stop
38 tappet
39a receptacle
40 crown wheel
41 crown tooth
42 latch element
43 spring element
44 distal end
45 proximal end
46 flange portion
50 dose setting sleeve
51 sleeve portion
52 shaft portion
53 connector
54 geared portion
56 geared portion
57 protrusion
60 base member
61 shaft portion
61 radial stop
62 outer thread
63 fastening element
64 bearing
65 cover portion
66 flange portion
67 window
68 window
69 retaining member
70 base member
71 recess
72 retaining structure
73 protrusion
74 sleeve portion
75 recess
76 receptacle
77 flange portion
78 bearing
79 fixing portion
80 display assembly
81 dose indicating member
81a central orifice
82 dose indicating member
82a central orifice
83 dose indicating member
84 annular groove
85 annular groove
86 display surface
87 display surface
87a recess
88 central gear
89 central gear
91 geared rim
92 display surface
93 retaining structure
93a recess
94 display wheel
95 geared section
96 geared section
97 pocket hole
98 tappet
99 pin
100 display wheel
101 geared section
102 geared section
103 pin
104 pocket hole
110 drive wheel
111 interlocking member
112 ratchet tooth
113 orifice
114 crown wheel
115 inner thread
116 latching element
117 protrusion 118 flange
119 crown tooth
120 dose setting member
121 arched portion
121a arched portion
121b arched portion
123 recess
124 protrusion
125 fastening element
126 flange portion
126a geared structure
127 gripping structure
128 sidewall
129 bottom portion
130 dose dispensing member
131 geared portion
131a pin
132 shaft portion
133 slot
134 proximal end phase
135 sidewall
136 spring element
140 last dose limiting member
141 protrusion
142 inner thread
143 radial stop
150 single dose limiting member
151 protrusion
152 thread
153 clicking element
154 radial stop
155 radial stop
160 piston rod
161 threaded portion
162 groove
163 pressure foot
210 transfer element
220 dose setting member
223 slot
228 sidewall portion
230 dose dispensing member
231 geared portion
232 shaft portion
233 stepped portion
235 sidewall portion
240 last dose limiting member
241 protrusion
242 inner thread
243a radial stop
243b radial stop
260 base member
261 shaft portion
262 outer thread

The invention claimed is:

1. A drive mechanism of a drug delivery device for dispensing of a dose of a medicament, the drive mechanism comprising:
an elongated housing extending in an axial direction;
a piston rod to operably engage with a piston of a cartridge to displace the piston in axial distal direction;
a first dose indicating member rotatably supported on a longitudinal axis;
a second dose indicating member axially adjacent to the first dose indicating member and rotatably supported on the longitudinal axis;
a dose setting sleeve extending in the axial direction, rotatably engaged with the first dose indicating member and axially extending through the first dose indicating member to rotatably engage with the second dose indicating member; and
a third dose indicating member rotatably supported on the longitudinal axis and comprising a third annular shaped display surface to visually indicate a zero dose configuration, wherein the third dose indicating member is configured to change its visual appearance when the drive mechanism returns into an initial configuration, wherein a drive sleeve is rotatably engaged with the second dose indicating member via a display wheel extending parallel and radially offset to the drive sleeve.

2. The drive mechanism according to claim 1, wherein the first and second dose indicating members are rotatably coupled or mutually engaged with each other only by way of the dose setting sleeve.

3. The drive mechanism according to claim 1, wherein the first dose indicating member comprises a first annular shaped display surface that flushes with a second annular display surface of the second dose indicating member.

4. The drive mechanism according to claim 1, wherein the first dose indicating member comprises a first central orifice axially flush with a second central orifice of the second dose indicating member.

5. The drive mechanism according to claim 4, wherein the dose setting sleeve is rotatably and axially connected to the drive sleeve serving as a distal extension of the dose setting sleeve, wherein the assembly of the dose setting sleeve and the drive sleeve extends through the first and through the second orifices of first and second dose indicating members.

6. The drive mechanism according to claim 1, wherein the display wheel is a second display wheel, wherein the dose setting sleeve is rotatably engaged with the first dose indicating member via a first display wheel extending parallel and radially offset to the dose setting sleeve.

7. The drive mechanism according to claim 6, wherein at least one of the first or second display wheels comprises two axially separated geared sections wherein one of the two geared sections meshes with an outer gear of the dose setting sleeve or with a tappet of the drive sleeve and wherein the other one of the two geared sections meshes with a central gear of the first or second dose indicating members.

8. The drive mechanism according to claim 6, wherein one axial end of at least one of the first and second display wheels is rotatably supported by the housing or by a base member connected to the housing and wherein an opposite axial end of the respective display wheel comprises a pin radially constrained in an annular and axially extending groove of first or second dose indicating members.

9. The drive mechanism according to claim 1, wherein the dose setting sleeve is axially displaceable relative to at least one of first and second dose indicating members between a proximal dose setting position and a distal dose dispensing position.

10. The drive mechanism according to claim 1, wherein the housing and/or a base member comprise a radially recessed or radially protruding retaining structure to engage with a corresponding radially protruding or radially recessed structure of the second dose indicating member for rotating the second dose indicating member in discrete steps.

11. The drive mechanism according to claim 6, wherein the third dose indicating member comprises an inwardly facing geared rim meshing with a radially outwardly extending tappet of the first display wheel.

12. The drive mechanism according to claim 1, wherein the third dose indicating member comprises an annular and radially inwardly facing retaining structure engaging with a radially outwardly extending retaining member of the housing or a base member.

13. The drive mechanism according to claim 1, wherein the first and the second dose indicating members at least in sections axially and radially abut.

14. A drug delivery device for dispensing of a dose of a medicament, the device comprising:
a drive mechanism comprising:
an elongated housing extending in an axial direction;
a piston rod to operably engage with a piston of a cartridge to displace the piston in axial distal direction;
a first dose indicating member rotatably supported on a longitudinal axis;
a second dose indicating member axially adjacent to the first dose indicating member and rotatably supported on the longitudinal axis;
a dose setting sleeve extending in the axial direction, rotatably engaged with the first dose indicating member and axially extending through the first dose indicating member to rotatably engage with the second dose indicating member;
a third dose indicating member rotatably supported on the longitudinal axis and comprising a third annular shaped display surface to visually indicate a zero dose configuration, wherein the third dose indicating member is configured to change its visual appearance when the drive mechanism returns into an initial configuration; and
a cartridge at least partially filled with the medicament and being arranged in the housing of the drive mechanism or in a cartridge holder fixed to the housing, wherein a drive sleeve is rotatably engaged with the second dose indicating member via a display wheel extending parallel and radially offset to the drive sleeve.

15. The device according to claim 14, wherein the first and second dose indicating members are rotatably coupled or mutually engaged with each other only by way of the dose setting sleeve.

16. The device according to claim 14, wherein the first dose indicating member comprises a first annular shaped display surface that flushes with a second annular display surface of the second dose indicating member.

* * * * *